US006432709B1

(12) United States Patent
Cohen-Haguenauer

(10) Patent No.: US 6,432,709 B1
(45) Date of Patent: Aug. 13, 2002

(54) ENCAPSIDATION CELL LINES AND EXPRESSION VECTORS FOR TRANSCOMPLEMENTATION OF DEFECTIVE RETROVIRAL VECTORS

(75) Inventor: Odile Cohen-Haguenauer, 35 rue Cortambert, 75116 Paris (FR)

(73) Assignee: Odile Cohen-Haguenauer, Paris (FR)

(*) Notice: Subject to any disclaimer, the term of this patent is extended or adjusted under 35 U.S.C. 154(b) by 0 days.

(21) Appl. No.: 08/564,989

(22) Filed: Nov. 30, 1995

(30) Foreign Application Priority Data

Nov. 30, 1994 (FR) .......................................... 94 14406

(51) Int. Cl.⁷ .......................... C12N 5/10; C12N 15/85; C12N 15/63

(52) U.S. Cl. ...................... 435/350; 436/69.1; 436/455; 436/320.1; 436/325; 436/352; 436/363; 436/366

(58) Field of Search .............................. 435/69.1, 172.1, 435/172.3, 320.1, 325, 350, 352, 363, 366, 455

(56) References Cited

U.S. PATENT DOCUMENTS

| 4,650,764 A | 3/1987 | Temin et al. ................ 435/350 |
| 5,124,263 A | 6/1992 | Temin et al. ................ 435/349 |

FOREIGN PATENT DOCUMENTS

| EP | 0 611 822 A2 | 2/1994 |
| EP | 0 632 129 A1 | 5/1994 |
| FR | 2707091 | 1/1995 |
| WO | WO 89/11539 | 11/1989 |
| WO | WO 90/02797 | 3/1990 |
| WO | WO 90/06757 | 6/1990 |
| WO | WO 91/12329 | 8/1991 |
| WO | WO 92/05266 | 4/1992 |
| WO | WO 94/05780 | 3/1994 |

OTHER PUBLICATIONS

Bosselman et al., Mol. Cell. Biol., vol. 7, No. 5, pp. 1797–1806, May 1987.*
Corrine Ronfort et al., "Defective Retroviral Endogenous RNA is Efficiently Transmitted by Infectious Particles Produced on an Avian Retroviral Vector Pakaging Cell Line", Virology 207:271–275 (Feb. 1995).
Corrine Ronfort et al., "Structure and Expression of Endogenous Retroviral Sequences in the Permanent LMH Chicken Cell Line", Poultry Science, 74, 127–135 (1995).
Idali Martinez et al., "Improved Retroviral Packaging Lines Derived from Spleen Necrosis Virus", Virology 208:234–241 (1995).
Francois Loic Cosset et al., "A New Avian Leukosid Virus–Based Packaging Cell Line that uses Two Separate Transcomplementing Helper Genomes", Journal of Virology, 64(3):1070–1078 (Mar. 1990).

Francois Loic Cosset et al., "High–Titer Packaging Cells Producing Recombinant Retroviruses Resistant to Human Serum", Journal of Virology, 69(12):7430–7436 (Dec. 1995).
M.E. Hoatlin et al., "Amplified and tissue–directed expression of retroviral vectors using ping–pong techniques", J. Mol. Med. 73:113–120 (1995).
Marc Sitbon et al., "Sequences in the U5–gag–pol Region Influence Early and Late Pathogenic Effects of Friend and Moloney Murine Leukemia Viruses", J. Virology 64(5):2135–2140 (May 1990).
Sylvia Perryman et al., "Complete Nucleotide Sequence of Freind murine leukemia virus, strain FB29", Nucleic Acids Research 19(24):6950 (Nov. 1991).
Rolf M. Flugel et al., "Nucleotide sequence analysis of the env gene and its flanking regions of the human spumaretrovirus reveals two novel genes", The EMBO Journal 6(7):2077–2084 (1987).
*Fields Virology*, Lippincott–Raven Publishers, Philadelphia, New York, 3rd Edition, vol. 1, pp. 40, 41, 1778–1786 (1996).
Kabat, D., "Molecular Biology of Friend Viral Erythroleukemia", *Current Topics in Microbiology and Immunology*, 148:1–42 (1989).
Watson et al. (1987) in : Molecular Biology of the Gene, Benjamin/Cummings Publ. Co., Menlo Park, CA, p. 313.
O. Cohen–Haguenauer, et al.; "Transduction of human CD34+ haemopoietic progenitors of various origin using an original retrovirus vector derived from Fr–MuLV and clinically relevant procedures"; *Hematology Cell Therapy;* 1996; pp. 205–206 (copy enclosed).
Joyner et al., *Prog. Cancer Res. Ther.*, 30:89–96 (1984).
Feldman et al., *J. Virology*, 63(12):5469–5474 (1989).
Holland et al., *PNAS USA*, 84: 8662–8666 (1987).
Velu et al., *Human Gene Transfer*, 219:273–274 (1991).
Bestwick et al., "Overcoming Interference to Retroviral Superinfection Results in Amplified Expression and Transmission of Cloned Genes", *Proc. Natl. Acad. Sci. USA*, 85:5404–5408 (Aug. 1988).
Danos et al., "Safe and Efficient Generation of Recombinant Retroviruses with Amphotropic and Ecotropic Host Ranges", *Proc. Natl. Acad. Sci. USA*, 85:6460–6464 (Sep. 1988).
Mclachlin et al., "Retroviral–Mediated Gene Transfer", *Progress in Nucleic Acid Res. and Molecular Biology*, 38: 91–135, (1990).

(List continued on next page.)

Primary Examiner—David Guzo
(74) Attorney, Agent, or Firm—Merchant & Gould P.C.

(57) ABSTRACT

The present invention relates to novel cell lines, so-called transcomplementation cell lines, which enable the packaging of recombinant retroviral RNAs carrying nucleotide sequences of interest. The present invention aims at transferring and expressing these sequences in eucaryotic target cells. The invention also related to expression vectors for the transcomplementation of defective retroviral vectors.

58 Claims, 14 Drawing Sheets-

OTHER PUBLICATIONS

Mulligan RC, "The Basic Science of Gene Therapy", *Science*, 260:926–931 (May 14, 1993).

Perryman et al., "Complete Nucleotide Sequenced of Friend Murine Leukemia Virus, Strain FB29", *Nucleic Acids Res.*, 19:6950 (Nov. 1991).

Perryman et al., "Retroviral Expression Vector pSFF DNA, Complete Sequence", *Nucleic Acids Res.*, cited in Genbank Database, Bethesda, US, GenBank ACC. No. (GBN):Z22761 (May 19, 1993).

Sitbon et al., "Hemolytic Anemia and Erythroleukemia, Two Distinct Pathogenic Effects of Friend MuLV: Mapping of the Effects to Different Regions of the Viral Genome", *Cell*, 47:851–859 (Dec. 1986).

Temin H.M., "Safety Considerations in Somatic Gene Therapy of Human Disease with Retrovirus Vectors", *Hum. Gene Ther.*, 1:111–123, (1990).

Sitbon et al., "Sequences in the U5–gag–pol Region Influence Early and Late Pathogenic Effects of Friend and Moloney Murine Leukemia Viruses", *U. Virol.*, 64:2135–2140 (May 1990).

Yu et al., "Open Reading Frame vpr of Simian Immunodeficiency Virus encodes a Virion–Associated Protein", *J. Virol.*, 64:5688–5693 (Nov. 1990).

Yu et al., "Self–Inactivating Retroviral Vectors Designed for Transfer of Whole Genes Into Mammalian Cell", *Proc., Natl. Acad. Sci.*, 83:3194–3198 (May 1986).

Fields, et al.; "Transformation by Molecular Mimicry and Insertional Mutagenesis: Friend Leukemia Virus"; *Virology;* pp. 323–324 (1996) (copy enclosed).

Ruan K.S., et al.; "Approach to a retrovirus vaccine: Immunization of mice against Friend virus disease with a replication–defective"; *Proc. Natl. Acad. Sci. US;* 89:24 (Dec. 15, 1992). Accession No. 93101695 Medline abstract of Proc. Natl. Acad. Sci. 89:12202–6. (copy enclosed).

Jolly, D., "Viral vector systems for gene therapy", *Cancer Gene Therapy*, 1(1):51–64 (1994).

Berger et al., Accession No. 86016806 Medline abstract of Proc. Natl. Acad. Sci. 82: 6913 (Oct. 1985). (copy enclosed).

Evans et al., Accession No. 80052056 Medline abstract of J. Virology 31: 133 (Jul. 1979) (copy enclosed).

* cited by examiner

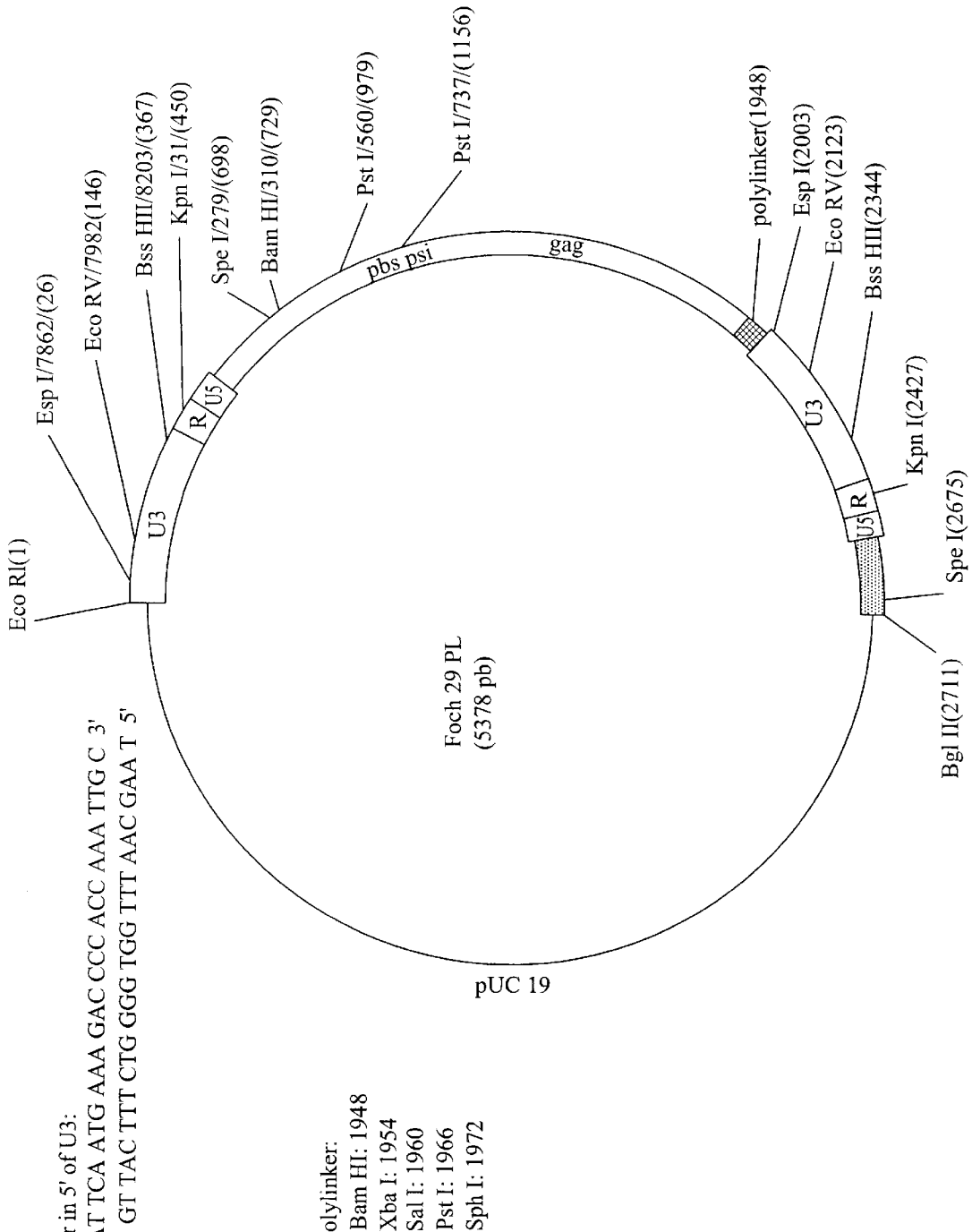

PURE LTR – ENV SPUMA

```
                             SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:1:

CTGCTGACGG GAGAAGAAAA AC                                                      22

(2) INFORMATION FOR SEQ ID NO:2:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: Genomic DNA (iii) HYPOTHETICAL: NO (iv) ANTI-SENSE: NO (v) FRAGMENT TYPE:
```

(vi) ORIGINAL SOURCE:

(xi) SEQUENCE DESCRIPTION: SEQ ID NO:2:

CCCGCTCAGA AGAACTCGTC                                                   20

(2) INFORMATION FOR SEQ ID NO:3:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:3:

GACGAGTTCT TCTGAGCGGG                                                   20

(2) INFORMATION FOR SEQ ID NO:4:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:4:

GATCTGAACT TCTCTATTCT TG                                                22

(2) INFORMATION FOR SEQ ID NO:5:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:5:

AATTCAATGA AAGACCCCAA ATTGC                                             25

(2) INFORMATION FOR SEQ ID NO:6:

(i) SEQUENCE CHARACTERISTICS:

```
          (A) LENGTH: 27 base pairs
          (B) TYPE: nucleic acid
          (C) STRANDEDNESS: single
          (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:6:

TAAGCAATTC GGTGGGGTCT TTCATTG                                        27

(2) INFORMATION FOR SEQ ID NO:7:

(i) SEQUENCE CHARACTERISTICS:
          (A) LENGTH: 8 base pairs
          (B) TYPE: nucleic acid
          (C) STRANDEDNESS: single
          (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:7:

CTAGTGCA                                                              8

(2) INFORMATION FOR SEQ ID NO:8:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:8:

TGACGGGAGA AGAAAAACAG CG                                             22

(2) INFORMATION FOR SEQ ID NO:9:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: Genomic DNA (iii) HYPOTHETICAL: NO (iv) ANTI-SENSE: NO
```

(v) FRAGMENT TYPE:

(vi) ORIGINAL SOURCE:

(xi) SEQUENCE DESCRIPTION: SEQ ID NO:9:

TAGGAGCAAC TGGCGATAGT GG                                            22

(2) INFORMATION FOR SEQ ID NO:10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:10:

GATTGCCAGA CTTGACTAAG CC                                            22

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:11:

TACCATCCGT AGGCAAGG                                                 18

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:12:

ATACCAATCA TTCCACCGCT CC                                            22

(2) INFORMATION FOR SEQ ID NO:13:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:13:

GTTGAGGTCT GTCTGGATAG CG                      22

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:14:

TAGGACCTGT AATAGACTGG                       20

(2) INFORMATION FOR SEQ ID NO:15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:15:

CCTTGAGAAC TCCAATCCTT CG                      22

(2) INFORMATION FOR SEQ ID NO:16:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Genomic DNA

```
        (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:16:

TAAGCAATTC GGTGGGGTCT TTCATTG                                               27

(2) INFORMATION FOR SEQ ID NO:17:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:17:

CTGCTGACGG GAGAAGAAAA AC                                                    22
```

ENCAPSIDATION CELL LINES AND EXPRESSION VECTORS FOR TRANSCOMPLEMENTATION OF DEFECTIVE RETROVIRAL VECTORS

The object of the invention is novel cell lines so-called transcomplementation cell lines which enable the packaging of recombinant retroviral RNAs carrying nucleotide-sequences derived from genes which in some instances might be of therapeutic interest (called transgenes), aiming at transferring and expressing these transgenes in eucaryotic target cells. The invention also relates to expression vectors for the transcomplementation of defective retroviral vectors.

The transfer of genes for therapeutic purposes or somatic "gene therapy" consists in inserting a "repairer" gene (transgene) in the somatic cells of a constituted organism in order to compensate for the dysfunction of an endogenous gene, or even to add a novel function for a therapeutic purpose. The resulting genetic change is likely to be transmitted to the daughter cells of the manipulated cell but it will not be inherited. The normal counterpart of altered DNA sequences is thus transformed into a medicine.

Various approaches are currently being explored in order to introduce into target cells genes or more generally, nucleotide sequences, for therapeutic purposes. These target cells might be directly the cells benefiting from the therapeutic intervention or cell-intermediate between the vector carrying the transgene and the cells to be treated.

Vectors currently under use for gene transfer into target cells are derived either from inactivated viruses, like retroviruses or adenoviruses, or else from macromolecular conjugates. Retroviruses usually address a target tissue including a stem cell pool which can be manipulated ex vivo; whereas, when the target tissue is made of terminally differentiated cells or embedded into an organ where architectural constraints have major functional consequences, like the lung, gene transfer must be performed in vivo, by means of recombinant adenovirus for instance.

Gene therapy finds applications in diseases as diverse as hereditary disorders due to the alteration of a single gene, such as Duchenne's myopathy, lyososomal diseases, cystic fibrosis or acquired disorders such as AIDS, cancers, thrombo-embolic disease or degenerative neurological diseases and inherited hematological diseases.

The development of retroviral vectors more efficacious than the existing tools constitute a major objective. In fact, retroviral vectors have demonstrated their efficacy in stably and permanently transferring genes where classically the cell-targets for the transfer undergo mitoses and ideally include a contingent of stem cells.

Current limitations stem from still inadequate infectivity of the viruses used and/or too moderate a level of transcription. Additional potential limitations deal with the safety of the transfer which to date remain unsatisfactory. This is both related to the risk for generation of replication-competent viruses and to the concomitant transmission of endogenous sequences which are generated by packaging cell-lines and may be packaged together with the defective recombinant virus genome.

The development of more efficacious and safer vector systems than those currently available is a matter of great significance.

Whenever the transgene to be expressed is delivered by means of a retroviral vector, the manufacture of stocks of retrovirus vector particles carrying along the transgene is a compulsory step preceding infection of target cells.

In order to achieve this, one should proceed with transcomplementation of the defective retrovirus vector carrying the transgene by the viral proteins, the corresponding encoding sequences of which being first deleted to be replaced by the transgene. This transcomplementation step can be performed passing through packaging cells. These cells are genetically engineered cells comprising the genetic material required for synthesis of viral components, in particular ENV envelope proteins, GAG nucleoproteins and POL reverse transcriptase, which allows for viral replication. The gag, pol and env genes are transfected into packaging cells through the transfection of the nucleic acid sequences which contain them, by means of a transcomplementation vector defective for the Psi-sequence which is otherwise mandatory to achieve virus packaging.

Expression of gag, pol and env genes within the packaging cells allows for further packaging of retroviral recombinant RNA sequences recombined with the transgene carried by a retroviral vector including the Psi-packaging sequences. Packaging may proceed following transcomplementation by the viral proteins encoded by the gag, pol and env sequences.

Currently available packaging cell lines are derived from cells of murine origin and harbour the following drawbacks:

1 Co-packaging of endogenous retroviral sequences (MCF, VL30, and even retrotransposons in some instances), together with defective constructs. Sequences which are co-packaged may as well integrate into the host genome following infection of gene transfer target cells.

2-Within these packaging cell lines, expression of complementing proteins is driven off a retrovirus LTR. Although third generation cell-lines make use of complementing retrovirus constructs including several mutation or deletion sites, maintaining LTR sequences might result in potential disadvantage; these sequences might well be able to induce genetic recombination with defective constructs to be complemented.

This has already been observed even from so-called third generation cell-lines where GAG and POL proteins encoding sequences, are being transfected separately from envelope coding sequences in order to reduce the likelihood for competent virus-generating combinations.

Envelope-encoding sequences currently under use to complement defective retroviruses towards gene transfer into mammalian cells and in particular of primate and human origin are amphotropic envelopes. It remains unsure that those cell-types that one wishes to infect towards gene therapy purpose would harbour enough receptors to amphotropic viruses.

All these elements justify efforts towards improvement in the safety of retrovirus-mediated gene transfer.

The object of the invention is to provide means to engineer novel packaging cell-lines to solve at least part of the abovementioned issues.

The cell-lines of the invention allow for the improvement of gene transfer safety since they are developed from cell-lines originating from animal species devoid of endogenous retroviral sequences identified to date and using, in a preferred embodiment non-viral promoters, to drive the expression of at least part of the viral complementing proteins, in particular inducible promoters for the conditional synthesis of defective vectors complementing proteins, especially of the envelope, upon request, whenever an infectious virus supernatant is to be prepared.

In addition GAG and POL proteins complementation is mediated by nucleotide sequences of a Friend retrovirus from which the vector has been built.

In order to implement the gag, and pol sequences are being transfected into the packaging-dedicated cell-line separately from envelope encoding sequences.

These cell-lines also lead to improvement in transfer efficiency through the use of envelope sequences, of human origin in particular, in order to circumvent the potential insufficient expression of the receptor to an amphotropic virus at the surface of human cell-targets for gene therapy; in particular potentially in case haematopoietic stein cells represent the targets.

According to a first embodiment, the object of the invention is an expression vector for the transcomplementation of a retroviral vector, which permits the transfer and/or integration within the genome of a target cell of a chosen nucleotide sequence (termed "transgenic sequence"), characterized in that it comprises:

a) a nucleotide sequence termed env, coding for the polypeptides derived from the envelope (ENV polypeptides) of a retrovirus of the spumavirus family, the ENV polypeptides permitting the packaging of retroviral RNAs, and b) transcription regulator signals controlling the expression of the env sequence, said expression vector being devoid of packaging signal sequences.

Retroviruses of the spumavirus (foamy virus) family are retroviruses one may be able to isolate from animal or human cell cultures.

A retrovirus named HSRV which belongs to the spumavirus family was isolated from a patient with nasopharyngeal carcinoma in 1971 (Hachong et al., J. Natl. Cancer Inst. 46, 299–307). The retrovirus HSRV has been cloned and sequenced and its sequence has been published by Flügel R M et al (the EMBO Journal, vol. 6, n°7, PP 2077–2084, 1987). This publication describes in particular the HSRV retrovirus envelope sequence.

Advantageously, the HSRV retrovirus envelope sequence used in the invention codes for a glycoprotein which can be recognized by a large number of surface receptors on human cells and in particular a glycoprotein which can make use of more receptors than would the amphotropic envelope glycoproteins, among a population of cells of human origin. According to an additional advantage of the invention, the envelope sequence under use harbour a tropism specific to human or primate for gene transfer in man or primate.

In particular, the HSRV-env sequence does interestingly harbour a tropism for human haematopoietic progenitor cells.

Besides haematopoietic stem cells, human primary cells such as fibroblasts or lymphocytes can be successfully targeted (lytic infection). Chronic infection by a defective virus has been evidenced in man within glandular epithelium or muscular tissues. Human originated cell-lines such as cells of epithelial or lymphocytic origin as well as HeLa can also represent appropriate targets. In rabbit, whatever the origin of primary cell tested, every one of them showed permissive to infection. The infection spectrum is thus very wide.

The expression of the env sequence being included in the transcomplementation expression vector can be driven off retrovirus transcription regulatory signals. In particular, these regulatory signals can be derived from retroviral LTR-sequence such as Friend retrovirus.

According to the present invention, the Friend virus strain under use is a strain identified as particularly virulent. The isolate 1–5 of the ecotropic Friend murine leukemia virus was obtained from long-term bone marrow cultures infected by the Friend virus complex which induces polycythemia (FV-P) (Mathieu-Mahul et al., 1982). The FB29 strain of F-MuLV derived from the isolate 1–5 (Sitbon et al., Cell, 47: 851–859, 1986) is responsible for cytolytic and leukemogenic effects on erythroid cells, leading to severe early hemolytic anemia followed by late erythroleukemia in susceptible mice inoculated at birth. The regions responsible for the erythroleukemia were localized in the U3 region of the viral LTR (Sitbon et al., 1986, Sitbon et al., PNAS USA, 88: 5932–5936, 1991). The principal determinant of the hemolytic anemia seems to depend on specific envelope sequences of the FB29 strain; its severity may be affected by three distinct regions, including a structural segment of the envelope, enhancer sequences of transcription localized in the U3 region and, finally, sequences of the U5-gag-pol regions (Sitbon et al., J. Virol. 64: 2135–2140, 1990). Furthermore, electron microscopical analyses of the viral particles have confirmed a significantly higher packaging capacity (1.5 to 2 log).

The spumavirus type retrovirus env sequence can thus be placed under the control of LTR sequence or of a part of the LTR sequence from the Friend virus FB29-strain sufficient to drive the transcription of the env-nucleotide sequence.

According to another embodiment of the invention, the expression vector for the transcomplementation is characterized in that the transcription regulator signals of the env sequence comprise a non-viral promoter. If the case arises, this promotor is followed either by the polyadenylation signal from SV40-virus or by another polyadenylation sequence.

The use of a non-viral promoter improves the safety characteristics of the thus engineered transcomplementation vector.

In addition, expression of the env-sequence can be triggered upon request, in case the promotor under use is of inducible type; i.e., the promotor can be activated by a molecule of choice, such as a pharmacologic compound in particular.

The gag and pol sequences which are being transfected separately can also be placed under the control of an inducible promoter.

Alternatively, transcription signals controlling the expression of the env- and/or expression of gag and pol-sequences can involve a conditional promotor the expression of which is restricted to defined cell-types.

One inducible type promotor suitable for the implementation of the invention is for instance, the promoter of the retinoic acid β receptor (RARβ promoter).

This promoter has been described by De Thé et al., in Nature, vol. 49, n° 6254, pp 177–180 dated Jan. 11, 1990.

A preferred expression vector for transcomplementation is such that the spumavirus family retrovirus env sequence is placed under the control of an HindIII-BamHI fragment of the retinoic acid β receptor, as described in De Thé's et al., abovementioned publication.

According to another embodiment of the invention, the expression vector for transcomplementation with respect to the envelope is characterized in that it comprises:

a) a nucleotide sequence termed env sequence, coding for the polypeptides derived from an envelope, for example an amphotropic envelope, for example the envelope 4070A of Moloney leukaemia virus (Mo-MuLV), and b) non-viral transcription regulator signals controlling the expression of the env sequence, containing, for example, an inducible or conditional promoter for example the RAR-β promoter.

According to a particular embodiment of the invention, the expression vector for transcomplementation is characterized in that the nucleotide sequence of the expression vector for transcomplementation, coding for the envelope polypeptides, is modified, for example by replacement of nucleotides by an arrangement of nucleotides coding for a polypeptide or glycoprotein recognized specifically by a defined cell type, or by the addition of such an arrangement.

According to another embodiment, the invention also provides for an expression vector for the transcomplementation of a retroviral vector, permitting the transfer and/or integration within the genome a target cell of a chosen nucleotide sequence (termed "transgenic sequence"), including:
  a) a nucleotide sequence termed gag coding for the polypeptides derived from a nucleoprotein (GAG polypeptides) of a retrovirus of the Friend retrovirus type,
  b) a nucleotide sequence termed pol coding for the derived polypeptides including a reverse transcriptase protein and an integrase (POL polypeptides) of a retrovirus of the Friend retrovirus type,
  c) non-viral transcription regulator signals controlling the expression of the gag and pol sequences, these signals containing, for example, an inducible or conditional promoter, for example the RAR-β promoter, and the abovementioned expression vector lacking encapsidation signals.

According to the invention, expression vectors for transcomplementation can be of an integrative type whether spontaneously or upon selection, or on the contrary, be episomal vectors.

The object of the present application also comprises a eukaryotic cell for the encapsidation of recombinant retroviral RNAs by transcomplementation, present on a retroviral vector which permits the transfer and the integration within the genome of a target cell of a chosen nucleotide sequence (transgenic sequence), the said cell being characterized that it exhibits the following properties:
  it is selected from the cells of animal species lacking endogenous retroviruses, preferably chosen from foetal or embryonic cells, in particular those of dogs or rabbits,
  it has a homogeneous morphology which is stable over time,
  it is not of tumour origin,
  it has the capacity to be selected in a minimum culture medium lacking $CO_2$, without prior transformation, and
  it has a rapid rate of multiplication.

According to the invention, the phrase 'without prior transformation' signifies that the cell does not benefit from the addition of oncogenic sequences, prior to its selection.

The cell morphology is homogeneous and stable with time, as long as it is not significantly altered over a time period of 6 months or more.

According to an attractive embodiment of the invention, a eukaryotic cell for the encapsidation of recombinant retroviral RNAs by transcomplementation, present on a retroviral vector permitting the transfer and integration within the genome of a target cell of a chosen nucleotide sequence (transgenic sequence), the said cell being selected from the cells of animal species lacking endogenous retroviruses, preferably chosen from foetal or embryonic cells, in particular those of dogs or rabbits, is obtainable by selection in accordance with the following method.
  a) culturing of chosen eukaryotic cells on ISCOVE rich medium (GIBCO) containing, in addiction, 10% of foetal calf serum and 10% of horse serum,
  b) passage of the cultured cells in DMEM medium containing 20% of foetal calf serum and culture of the cells for one month in a medium without $CO_2$,
  c) selection of the cells having a rapid rate of multiplication (accelerated kinetics),
  d) passage of the selected cells in DMEM medium containing 10% of foetal calf serum,
  e) passage of the cells recovered in step d) in DMEM medium containing 10% of newborn calf serum (HyClone),
  f) recovery of the cells selected at the end of step e).

A eukaryotic cell can accordingly be the foetal dog cell designated DOGOM1 deposited at the CNCM on Nov. 30, 1994 under number 1-1496.

The dog foetal cell thusby obtained satisfies the following selection criteria; it lacks endogenous retroviruses; the adhesive characteristics of the cell are satisfactory; it has a rapid growth rate and its morphology is homogeneous and stable this dog foetal cell can also easily be transfected and is permissive to high range passagings (testing for intensive artificial passage-rate); it is capable of supporting a LTC-IC test (Long term culture initiating cells) as described in the experimental section.

From the above selected cells, genetically engineered cells permitting the encapsidation of retroviral RNAs can be prepared for instance by transfection in the above described cells or by their infection with the nucleotide sequences coding for the transcomplementation polypeptides or glycoproteins, the said sequences being supplied by means of at least two vectors or even at least three vectors. For example, on the one hand, a transcomplementation vector consisting either in a plasmid vector or a retroviral vector capable of expressing the env sequences encoding for the polypeptides derived from the envelope of a retrovirus of the spumavirus family can be used; and on the other hand, a vector, for instance ail expression plasmid-vector or a retroviral vector for the transcomplementation of the gag and pol nucleotide sequences of a retrovirus of the Friend virus type.

According to another embodiment of the invention the transcomplementing cells are xenogeneic, allogeneic or autologous cells which are likely to permit in vivo delivery of an infectious defective vector into a patient. In the latter case the transcomplementing cells may represent the cell-target for infection with the retroviral vector. For example, endothelial, muscle or stromal cells can be used.

The present application concerns a recombinant cell permitting the encapsidation of recombinant retroviral RNAs by transcomplementation (transcomplementing recombinant cell), characterized in that it is a cell replying to the above given definition and it is genetically engineered, for example, by transfection or infection with:
  on the one hand, a first expression vector for the transcomplementation of a retroviral vector permitting the transfer and/or integration within the genome of a target cell of a chosen nucleotide sequence (termed "transgenic sequence"), comprising the following transcomplementing sequences:
    a) a nucleotide sequence termed gag sequence coding for the polypeptides derived from a nucleoprotein (GAG polypeptides) of a retrovirus of the Friend retrovirus type,
    b) a nucleotide sequence termed pol sequence coding for the derived polypeptides including a reverse transcriptase and an integrase (POL polypeptides) of a retrovirus of the Friend retrovirus type, and
    c) transcription regulator signals controlling the expression of the gag and pol sequences,
  the abovementioned transcomplementation vector lacking packaging signals and, on the other hand, a second expression vector for the complementation with respect to the env proteins comprising a nucleotide sequence coding for the envelope polypeptides and elements for regulation of the expression of this sequence.

According to the invention, a 'virus of the Friend virus type' is a virus the gag, pol, and env coding sequences of which have homologies with those of the Friend virus following alignment to achieve packaging of retroviral RNA as described in the present application.

According to a first embodiment of the invention, the nucleotide sequence encoding for one or several envelope polypeptides is derived from a retrovirus of the spumavirus family. It might for instance involve sequences derived from HSRV.

According to another embodiment of the invention, the nucleotide sequence coding for envelope glycoproteins is derived from the 4070A sequence of Mo-MuLV virus.

The various cell-lines are genetically engineered by means of sequential transfections along the principle of third generation packaging cell-lines; i.e., using fragmentation in two or even three or more, distinct parts of the sequences encoding GAG, POL and ENV complementing proteins and of their associated regulatory elements. This procedure reduces the potential for genetic recombination which could generate replication competent virus particles.

According to one embodiment of the invention, the packaging cell-lines of the invention are in other words, characterized in that they comprise:

a) a nucleotide sequence termed gag sequence coding for the polypeptides derived from a nucleoprotein (GAG polypeptides) of a retrovirus of the Friend retrovirus type, b) a nucleotide sequence termed pol sequence coding for the polypeptides derived from a reverse transcriptase and from an integrase (POL polypeptides) of a retrovirus of the Friend retrovirus type, c) transcription regulator signals controlling the expression of the gag and pol sequences, d) a nucleotide sequence termed env sequence, coding for the polypeptides derived from the envelope (ENV polypeptides) of a retrovirus of the spumavirus family, the ENV polypeptides permitting the encapsidation of retroviral RNAs, and e) transcription regulator signals controlling the expression of the env sequence.

The above described packaging cells are in addition intended to be transfected by a retroviral vector carrying the chosen desired transgenic sequence which should be expressed in a target cell upon infection with the supernatant of the packaging cells.

According to another embodiment, the object of the invention is a packaging cell characterized in that it comprises:

a) a nucleotide sequence termed gag sequence coding for the polypeptides derived from a nucleoprotein (GAG polypeptides) of a retrovirus of the Friend retrovirus type, b) a nucleotide sequence termed pol sequence coding for the polypeptides derived from a reverse transcriptase and from in integrase (POL polypeptides) of a retrovirus of the Friend retrovirus type, c) transcription regulator signals controlling the expression of the gag and pol sequences and, d) a nucleotide sequence termed env coding for the polypeptides derived from an amphotropic envelope, for example the envelope 4070A of Moloney leukaemia virus (Mo-MuLV), e) transcription regulator signals controlling the expression of the env sequence.

Advantageously, the packaging cell-lines of the invention lack helper virus and endogenous viruses, thus providing with improved safety conditions.

The GAG, POL, ENV polypeptides which are mentioned in this application either do correspond to all of the polypeptides and/or glycoproteins expressed by the virus nucleotide sequences gag, pol, env; or to a part of these polypeptides and/or glycoproteins; or to modified variants through a truncation process in particular, in case those permit achievement of the sought transcomplementation towards infection of the cell targets.

A particularly attractive cell according to the invention is characterized in that it is the cell DOGOM1 deposited at the CNCM under number I-1496, recombined on the one hand with the gag, and pol nucleotide sequences of Friend retrovirus strain FB29 under the control of the transcription signals contained in the LTR sequence of the Friend retrovirus strain FB29, and recombined on the other hand with the env nucleotide sequence of a retrovirus of the spumavirus type under the control of an inducible promoter, for example the RARβ promoter.

Control of the sequence coding for the spumavirus envelope by means of an inducible promoter should prevent a potential lytic effect in transfected cells as a consequence of expression of spumavirus sequences.

Another attractive recombinant transcomplementing cell according to the invention is characterized in that the transcription signals included into the LTR-sequence of the Friend FB29-retrovirus which control the expression of gag and pol sequences are replaced by a non-viral promoter followed by SV40-virus polyadenylation signal or an alternative polyadenylation sequence.

The gag and pol sequences can thus be placed under the control of for example an inducible promoter such as RAR-β.

According to another embodiment, the subject of the invention is recombinant transcomplementing cells for the packaging of retroviral RNA, characterized in that they comprise the abovementioned gag and pol sequences, under the control of an or else a conditional promoter; and an env sequence, for example amphotropic and for example derived from the 4070A Moloney virus env sequence under the control of an inducible or a conditional promoter as well.

According to a particular embodiment of the invention, the transcomplementing cell is characterized in that the nucleotide sequence of the expression vector for transcomplementation, coding for the envelope polypeptides, is modified, for example by replacement of nucleotides by an arrangement of nucleotides coding for a sequence of a polypeptide or glycoprotein recognized specifically by a defined cell type, or by the addition of such an arrangement.

The thus obtained recombinant cells are in addition, transfected with a retroviral vector for the expression and/or transfer and/or integration within the genome of a target cell of a chosen nucleotide sequence (transgenic sequence), the said retroviral vector being advantageously constructed starting from the FB29 strain of Friend retrovirus.

The retrovirus vector thus can be constructed in placing the transgenic sequence to be expressed under the control of the LTR sequence, while the gag-, pol-, env-encoding sequences being deleted at least in part; and the packaging sequence being included inside the vector construct.

A useful vector to be used for the transfection of the abovementioned transcomplementing cells is the vector pFOCH29 shown in FIG. 1 and deposited at the CNCM under No. I-1326 on Jun. 30, 1993. The transgenic sequence to be expressed into the target cells is inserted at a site which is non-essential for its replication.

Other retrovirus vectors can be used. In particular pFOCH29 derivatives will first be considered but if the case arises deleted at least in part amidst the LTR sequences and for example of the U3 domain of the LTR sequence.

Another vector is the vector pFOCH29 PL shown in FIG. 2.

According to the invention, any defective retroviral vector which can be efficiently pseudotyped passing through the abovedefined complementation cell-lines, can be used for transgene gene transfer purposes.

A transgenenic nucleotides sequence is a nucleotidic sequence which is not naturally part of the vector genomic sequences, and in particular of the sequences which control expression, cloning or gene transfer. It may be either a natural or a synthetic sequence, especially a hybrid sequence.

'Transfer of transgenic nucleotides sequence' means integration of a sequence carried by the vector, within the genome, or in a satellite of the latter, of a target cell transduced with this vector. Such a transfer might result from a recombination, in particular homologous recombination.

The retroviral vector can therefore mediate the permanent expression of an exogenous nucleotide sequence through the modified, genome of a target cell; the exogenous sequence being selected according to its ability to undergo integration into the genome of the target cells.

The abovedefined defective vectors which carry the transgenic sequence or the plasmid-expression vectors which carry the gag, and pol sequences on the one hand and the env sequences on the other hand for complementation towards packaging, are introduced inside the packaging cell-line preferably by transfection or electroporation for example. This transfection can result in formation of viral particles which are suitable for achieving recombination following target cell transduction. This is performed towards cloning transfer or expression of the transgenic sequence included in the vector.

The sequence of therapeutic interest which can be introduced in target cells by means of the vectors and the packaging cell-lines of the invention are for example sequences which correspond to the normal equivalent of a non-functional gene in the context of a particular disorder; or else to an antisense sequence or to a dominant negative mutant of a particular gene; or to a sequence encoding for a functional inhibitor of a gene; or else to a reporter marker gene; or to a regulatory gene or a regulatory sequence of a particular gene; or to a gene which might confer a new function to target cells.

The invention does provide with appropriate means for gene therapy of cancer either through gene correction or improvement of strategies intended for the destruction of tumor cells. According to the first technique one can aim at correcting either inherited mutations in the context of inherited predisposition to cancer or signal transduction dysfunction, such as rasoncogene- and homologues-pathways; dysfunction resulting in oncogenes activation, dysfunction which results in tumor suppressor genes inhibition as well as correction of abnormalities which favour genetic instability or else which involve DNA-repair.

According to the second strategy, the invention can be advantageously operated in order to activate prodrugs such as making use of Herpes virus thymidine kinase gene which transforms either Ganciclovir or Acyclovir into cytotoxic drugs or else making use of the Cytosine deaminase gene which transforms a 5-fluorouracile precursor into an active drug; or else in order to induce or stimulate the immune system through genetic engineering of tumour cells by means of cytokines genes for example; or through engineering of antigen-presenting cells or their precursor (haematopoietic stem cells) or through immune effector cells-, T-cells-, B-cells-, LAK cells- or TIL cells engineering.

As for correction of genetic disorders, of anemias, the invention can be applied to the correction of inborn errors of metabolism, of haemoglobinopathies, such as thalassemias or drepanocytosis, of haemostasis and coagulation disorders, or else correction of inherited myelination disorders or myopathies.

The invention can also usefully be applied to either therapy or prevention of infectious disease such as AIDS; to cardiovascular diseases; to disorders of the lung, skin, liver and digestive tract, neuromuscular, central nervous system, pleura and peritoneum, etc.

According to another embodiment of the invention the transgenic sequence encodes for an antigen or a genetic determinant or an antiidiotype.

According to another embodiment of the invention the transgenic sequence encodes for an antibody, in particular a single chain antibody including especially variable sequences which are responsible for antigen recognition.

A vector containing such an antigenic determinant could potentially be used as a permanent or transient vaccine or if the case arises in the context of a therapeutic protocol, for example in order to elicit an immune response.

The tools of the invention are also suitable for performing vaccination of patients against pathogens or adventitious agents whether permanently or transiently.

The transfer might be performed through transduction of either cells, tissues, organs or organisms.

Suitable cell targets for implementing the invention are for example fibroblasts, endothelial cells, mesothelial and mesenchymal cells, skin cells among which keratinocytes, liver cells among which hepatocytes, muscle cells, accessory cells of the central nervous system, glial cells, oligodendrocytes, astrocytes etc. . . . ; epithelial cells among which urotheliuma, glandulary epithelia among which that from mammary gland, pulmonary epithelium, digestive tract epithelium as well as cell-lines whatever their origin.

FIG. 1: A: restriction map of FOCH29 vector. Numbering according to FB29 strain sequence Cla→U3 140 (7702–7845)
U3→R 410 (7845–8255)
R→CBS 145 (0–145)
PvuII→BamHI 208
PvuII→PvuII 1098
PvuIIMT→PvuII 1669
BsmAI→55/150/765/1766/2531/2684

B: restriction map of FOCH29 vector in which sites are indicated following numbering according to FB29 strain sequence as of FIG. 1A and with the numbering which belongs to the construction as such (numbers between brackets).

FIG. 2 restriction map of FOCH29-PL vector.

FIG. 3: A, B: restriction maps of the plasmid-vector including the LTR-FB29 del Psi-gag/pol FB29.

FIGS. 4A and 4B contain restriction maps of the plasmid-vector including the RAR-β-SD-Del Psi gag/pol FB29.

FIG. 5: construction of the plasmid-vector 'Pure LTR' including the 4070A amphotropic envelope.

EXAMPLES

A) PREPARATION OF THE RETROVIRAL VECTOR pFOCH29

MATERIALS AND METHODS

Figure 1A:
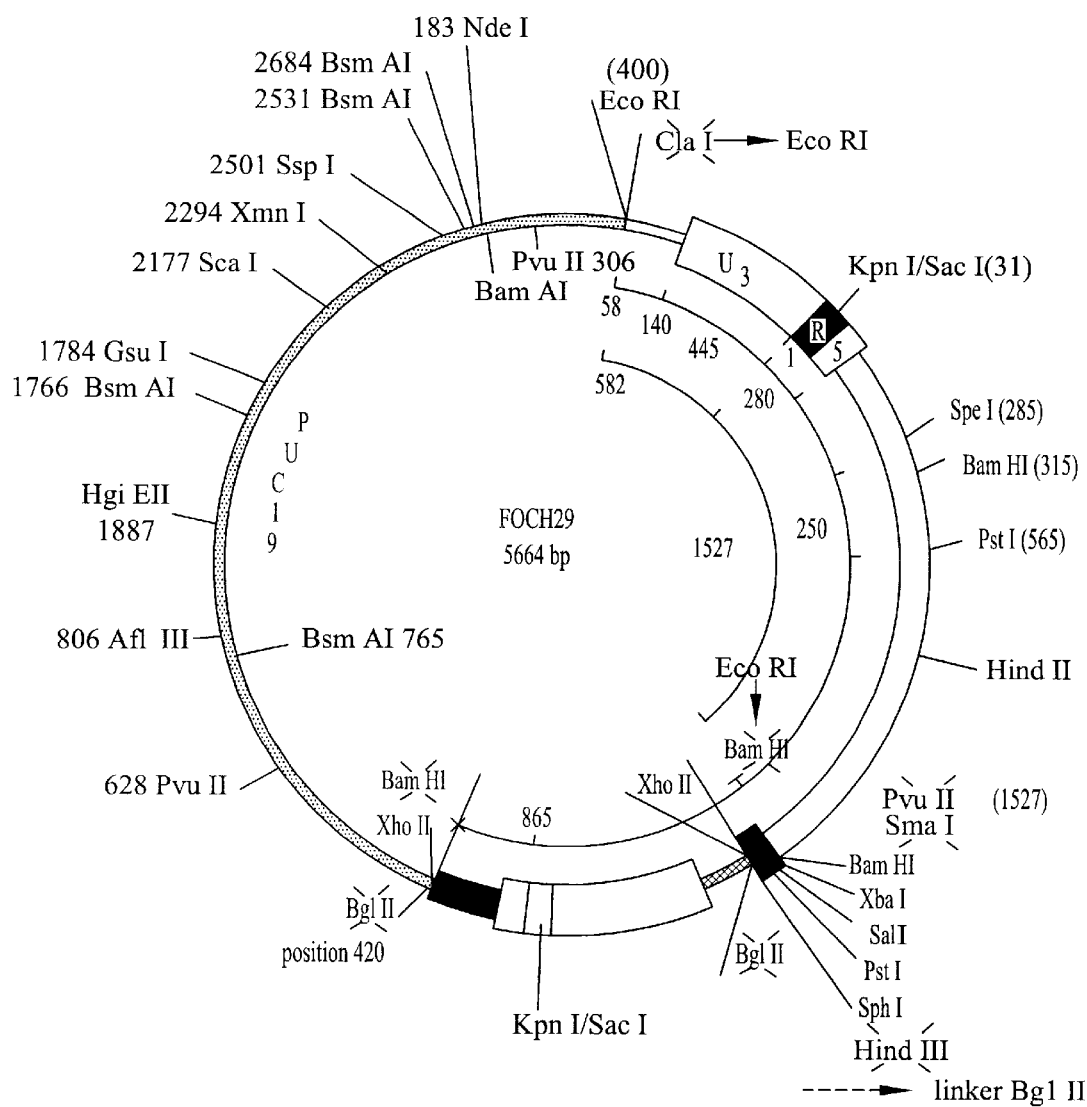
Figure 1B:
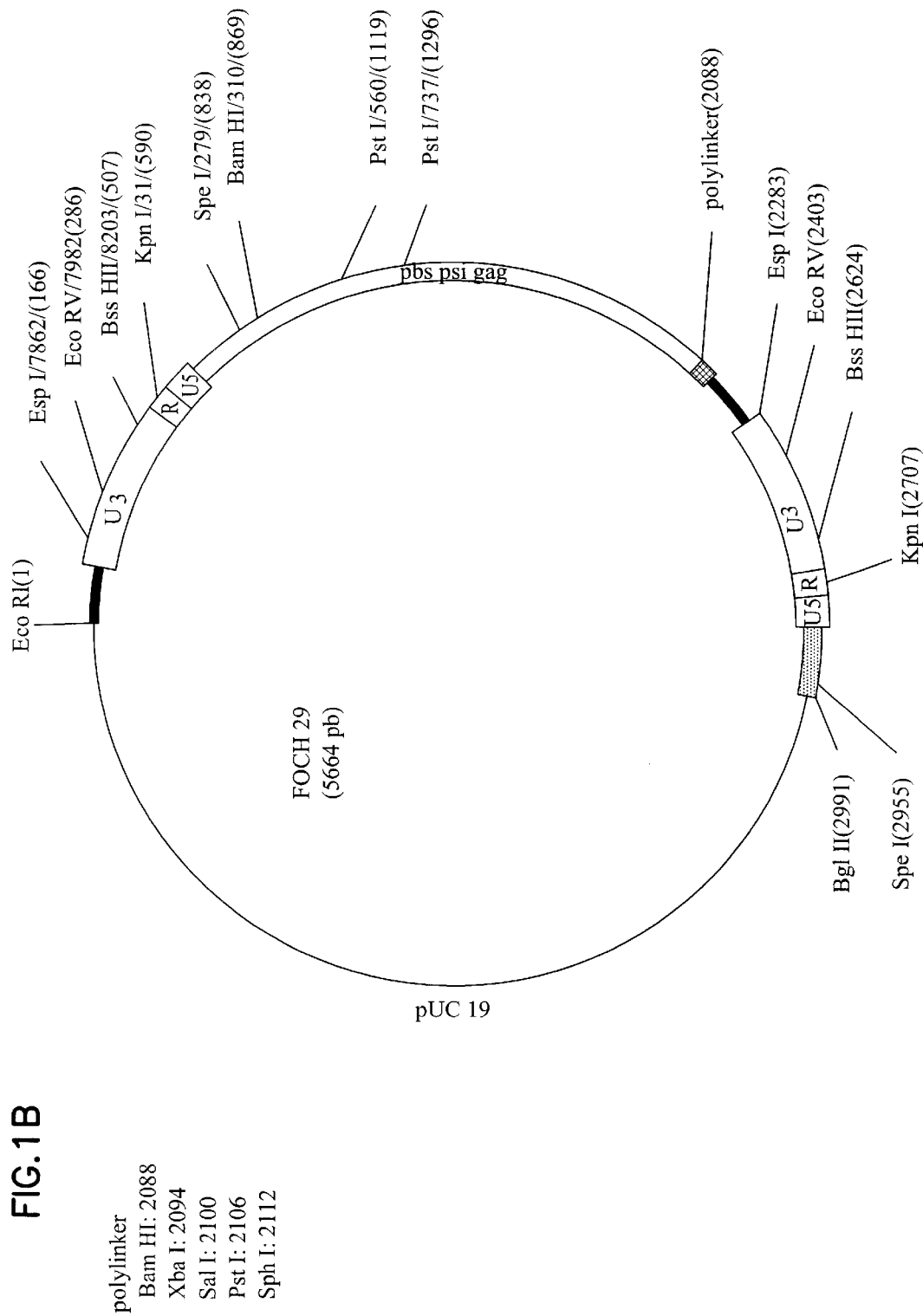

1 Source of the viral genomic material

The genomic DNA of the provirus was cloned in pBR322 (Sitbon et al., 1986). After replacement of the ClaI site at 7702 of the viral sequence by a EcoRI site, the EcoRI-PvuII fragment of 2110 base pairs (bp) containing all of the viral Long Terminal Repeat (LTR) was subcloned at the EcoRI and SmaI sites of the polylinker of pUC19.

2 Construction of the retroviral vector FOCH29

The HindIII site of the polylinker of pUC19 containing the EcoRI-PvuII fragment was replaced by a BglII site, after opening by HindIII, filling in with the long fragment of *E. coli* DNA polymerase (Klenow fragment) and ligation with a BglII adaptor not recreating the HindIII site; the BglII site was introduced to receive a BamHI—BamHI fragment of 865 bp containing a second copy of the native LTR of the Friend virus destined to constitute the downstream LTR (or 3' LTR). This BamHI—BamHI fragment was isolated by replacing the EcoRI site of pUC19 by a BamHI site upstream by means of a linker not recreating the EcoRI site after filling in of the ends by the Klenow fragment of the DNA polymerase; the BamHI site downstream is endogenous to the viral sequence.

This fragment was thus introduced by ligation with the backbone (pUC19) whose opening by BglII made it possible to combine the cohesive ends with the ends generated by BamHI. The resulting plasmid is called pFOCH29.

3 Introduction of a marker gene

The BglII-BamHI cDNA fragment (1500 bp) of the gene for neomycin resistance derived from the retrotransposon Tn5 (NeoR) was introduced between the two viral LTRs after ligation of the three fragments: pUC19-5' LTR BglII, NeoR BglII-BamHI and 3' LTR BamHI-BamHI. The resulting plasmid is called pFOCH29-Neo.

4 Transfection of packaging lines psi-CRIP and infection of fibroblasts

The plasmid pFOCH29-Neo was introduced into the amphotropic packaging line psi-CRIP described by Danos et al. (1988) by transfection using calcium phosphate precipitation according to the standard procedure without DNA carrier; 10 micrograms of plasmid were deposited on a culture dish 35 mm in diameter on which $5 \times 10^4$ cells were seeded the day before.

The psi-Crip cells were grown in Dulbecco's modified Eagle's (DMEM, Gibco-BRL) supplemented with 10% newborn calf serum (Hyclone). Two days after transfection the cells were trypsinized, diluted 1/20 and subjected to selection in the presence of geneticin at a final concentration of 1 milligram (mg) per milliliter (ml) of culture medium. The colonies which appeared after 12 days were selected and reimplanted on 24-well culture dishes at a concentration of one clone per well.

The cell culture supernatant of a well which had reached congruence was taken, filtered through a 0.45 μm filter to remove cells in suspension and used to infect mouse fibroblasts (NIH3T3) seeded identically on 24-well culture plates in the presence of polybrene at a concentration of 8 ug/ml. The NIH3T3 were grown in DMEM supplemented with 10% fetal calf serum (FCS). Viral integration was analysed by PCR on a lysate of NIH3T3) which had reached confluence.

5 Polymerase chain reaction (PCR)

The lysate supernatant Of the confluent NIH3T3 in a well of the 24-well culture plate was recovered in 100 μl, 10 μl of which were used in the PCR reaction, which is carried out in the following buffer 10X standard PCR buffer including 25 mM of $MgCl_2$ (Perkin-Elmer/Roche MS); 100 nanograms (ng) of each primer, 2 ul of dNTPs 10 mM (equimolar mixture of each dNTP at an initial concentration of 10 mM, i.e. 2.5 mM of each), 2 units of cloned Taq polymerase (Perkin-Elmer/Roche MS) for 40 cycles, a single unit for 25 cycles; in a final volume of 50 ul.

Two pairs of primers were used.

The oligonucleotide sequences used are:

1°) for the first pair:
5'CTGCTGACGGGAGAAGAAAAAC-3' SEQ ID NO:1 5'CCCGCTCAGAAGAACTCGTC-3' SEQ ID NO:2

2°) for the second pair:
5'GACGAGTTCTTCTGAGCGGG-3' SEQ ID NO:3
5'GATCTGAACTTCTCTATTCTTG-3' SEQ ID NO:4

The size of the amplified sequences is in the case of the first pair, end-gag/two thirds proximal NeoR gene: 900 bp; and for the second pair, one third distal NeoR gene/proximal half of 34 LTR: 610 bp.

Denaturation 5 min at 94° C.; 40 cycles oil GeneAmpPCR 9600 with denaturation 30" at 94° C.; annealing 15" at 55° C. and elongation 30" at 72° C.; followed by a terminal elongation step of 10 min.

The samples (15 ul out of 50 ul) were deposited on a 1.2% agarose gel (Seakem, FMC) and were subjected to horizontal electrophoresis for 45 min at 80 volts; the detection of the signal based on the analysis of the intensity of ethidium bromide (BET) fluorescence.

6 Determination of the infective titers

Each of the clones tested for its capacity to infect NIH33T3) was amplified and optionally frozen prior to the analysis of the efficiency of infection by PCR.

After PCR two principal clones were selected and amplified in order to infect NIH3T3 according to a standard procedure.

1 ml of 16 hours culture supernatant was taken at congruence from each producing clone on a dish 35 mm in diameter, filtered through a 0.45 um filter in order to remove productive cells in suspension. The supernatant was placed in contact with NIG3T3 cells at 50% congruence on culture dishes of the same diameter (35 mm) in the presence of polybrene at a concentration of 8 ug/ml of medium. The cells were incubated for about 2h30 at 37° C., the medium was shaken every half hour. Three volumes of fresh medium were added after 2h30.

INFECTIVE VIRAL TITERS

Successive dilutions of the primary supernatant were used to infect NIH3T3 cells; undiluted supernatant and supernatant at dilutions 1/10, 1/1000 and 1/100000. Two days after infection the cells were trypsinized, subcultured at about 1/20 on three culture dishes 100 mm in diameter and placed under selection by the addition of geneticin (1 mg/ml) to the supernatant.

This experimental procedure was made more stringent in the sense that: on the one hand, the drug was added very quickly after the infection; and, on the other, the direct placing in selection without trysinization of the cells prevents the artificial multiplication of the number of resulting colonies, the daughter cells derived from an infected cell remained grouped together and formed only one colony In situ. Conversely, when the cells are trypsinized, the daughter cells spread on the recipient culture dish and form artificially independent colonies which, if they are counted, artificially multiply the liter.

SOUTHERN BLOT

Two days after infection by the undiluted supernatant the NIH3T3 were trypsinized, subcultured at about 1/20 on three culture dishes 100 mm in diameter, one of which is subjected to selection by geneticin.

At congruence the genomic DNA of the infected cells for each of the two clones after or without selection is extracted then quantified.

The DNA was digested by two restriction enzymes, PstI and KpnI, in order to carry out a Southern blot. After control of the quality Of the digestion and the deposition of an equivalent quantity of DNA in each well, the transfer was carried out on a nylon Hybond N membrane (Amersham). Hybridization was performed with a probe which included all of the viral LTR sequences flanked by 100 bases upstream and 100 bases downstream. The probe was labelled by primer extension (Feinberg and Vogelstein, 1983, 1984) with alpha-$^{32}$ P labelled dCTP of specific activity of $5\times10^8$ cpm/ug.

The hybridization was carried out in a medium consisting of 50% deionized formamide; 5×SSEP; 1×Denhardt's, 5% dextran sulfate and 0.2 mg/ml of sonicated salmon DNA for 20 hours at 42° C. Brief rinsings, were carried out in a solution of low stringency: 2×SSEP/0.1% SDS, 5 min at room temperature and 10 min at 65° C., followed by exposure for 3 days to Kodak-XAR-5 films at −80° C. with LI-Plus intensifying screens (Dupont-NEN).

7 Search for the production of helper virus

This search was carried out by a mobilization test oil 3T3BAG lines Dallas et al., 1988; Dallas 1991).

The 3T3BAG cells were initially infected by the undiluted supernatant of infected packaging lines. Several successive cycles of infection of unexposed 3T3BAG with the supernatant of previously infected 3T3BAG were carried out to sensitize the test.

RESULTS

1 Construction of the retroviral vector FOCH29

The viral strain FB29 of the Friend murine leukemia virus was isolated (Mathieu-Mahul et al., 1982) and the genomic DNA of the integrated provirus was cloned in pBR322 (Sitbon et al., 1986). This genomic DNA has been completely sequenced (Perryman et al., 1991). The genomic fragment ClaI-PvuII of 2120 bp was cloned in pBR322. This fragment contains the last nucleotides of the sequence coding for the p15E of the viral envelope, all of the Long Terminal Repeat (or LTR) and ⅗ of the gag sequence. It constitutes the matrix of the architecture of the vector.

After replacement of the ClaI site by a EcoRI site the EcoRI-PvuII fragment was subcloned in the EcoRI-SmaI of the polylinker of pUC19. This clone was, on the one hand, kept intact to form the basic architecture of the vector including the upstream LTR or 5' LTR, the binding site for the initiator of viral transcription (primer binding site or PBS), the packaging sequence, the gag sequences and the segment of the polylinker of pUC19 treated by EcoRI/SmaI digestion, destined for the insertion of the genes of interest.

On the other hand, a BamHI—BamHI fragment was derived by replacing upstream the EcoRI site by a BamHI site, and by taking advantage downstream of the endogenous BamHI site of the virus, situated immediately downstream from the donor splice site. This fragment was introduced into the basic framework of which the HindIII site of the polylinker has been replaced beforehand by a BglII site generating ends cohesive with those generated by the BamHI enzyme.

The marker gene derived from the retrotransposon Tn5 which confers resistance to neomycin (NeoR) was introduced between the two LTRs. After transformation on a strain of supercompetent bacteria of dominant negative recombinase phenotype in order to prevent possible reorganization of the sequences present, the transformants of the expected configuration were selected on the basis of the extended restriction map exploring all of the construction. One of them, designated pFOCH29, was then amplified and purified in order to have available an adequate source of material destined for the transfection of helper lines producing viral particles.

2 Isolation of producer clones of defective virus

Transfection of psi-CRIP packaging lines: the plasmid pFOCH29-Neo was introduced in to the amphotropic packaging line psi-CRIP described by Dallas et al. (1988) by transfection sing calcium phosphate precipitation according to the standard procedure without carrier DNA.

After subjection to selection by geneticin, 40 of the colonies formed were taken and the culture supernatant was used to infect mouse fibroblasts (NIH3T3)). The primary selection process of a series of the most highly productive clones of packaged defective viral particles was based on the use of the gene amplification procedure by means of the polymerase chain reaction. The viral integration is analysed by PCR on a lysate of NIH3T3 which had reached confluence.

Two distinct PCR primer couples were used: 1° a first couple amplifying the terminal segment of the gag sequences included in the construction and the proximal two thirds of the gene for neomycin resistance; 2° a second primer couple amplifying the distal third of the gene for neomycin resistance and the half of the downstream LTR (3').

Four clones were selected on the basis of a more intense PCR signal than the other 36; repetition of the procedure confirmed the initial data indicating that for two clones the signal was emitted markedly more intensely. These two clones were amplified and the culture supernatant of the producer cells was then used to infect NIH3T3 on a larger scale for the purpose of evaluating the efficiency of the construction in quantitative terms.

3 Evaluation of the producer clones

Quantitative PCR

A semi-quantitative analysis by PCR was performed by using the primer couple amplifying the region corresponding to the distal third of the NeoR gene up to the median part of the downstream LTR (3' LTR). For each clone 1 µg and 3 µg of genomic DNA extracted from NIH3T3 cells by an undiluted supernatant after or without selection by neomycin were used. Each assay was performed in duplicate. Several dilutions of the plasmid pFOCH29-Neo were tested in parallel calculated such that they correspond to 0.1, 0.5 and 1 copy of transgene for the equivalent of 1 ug of genomic DNA, i.e. 0.115 pg, 0.575 pg and 1.15 pg respectively for a plasmid of 7164 bp.

The PCR was carried out for 24 cycles, which still corresponds to an exponential phase of the reaction. The reading was performed by computerized densitometric analysis (Cybertech) of ethidium bromide fluorescence.

In the case of the first clone a significant difference was observed between the intensity of the signal obtained from selected and non-selected infected cells; more clear-cut on the samples of 1 μg (70% of the signal with respect to the selected) than on those of 3 μg for which the detection system was saturated by the intensity of the signal.

In the case of the second clone, there is no difference in intensity of the signal between selected and non-selected cells, neither for the 1 μg samples nor the 3 μg samples. This suggests that a percentage of the NIH3T3 cells close to 100% had been infected by the undiluted supernatant of this producing clone. The high degree of infectivity of this clone was moreover suspected by the observation of an absence of cell mortality when the NIG3T3 infected with the culture supernatant were subjected to selection by neomycin.

Southern Blot

The DNA of the infected NIH3T3 cells was subjected to hydrolysis by two restriction enzymes: KpnI and PstI. Tile expected size of the bands after viral integration varies depending on the probes used. In the case of the enzyme KpnI which cuts Within the LTRs and in the middle of the polylinker of pUC19, a LTR probe reveals a constant fragment size of 3610 bp and two fragments of variable size depending on the proximity of the endogenous genomic KpnI sites to the integration site; a probe derived by PCR with the primers distal third NeoR/proximal LTR segment, a fragment of the same size (3610 bp) is expected and only one of the two other fragments variable from one integration to another.

In the case of the enzyme PstI which Cuts twice in the median part of gar, and once in the polylinker of pUC19, after integration the fragments identified by the former two probes should be of variable size, a probe generated by PCR from the second primer couple identifies a constant fragment of 790 bases.

Several dilutions of the plasmid pFOCH29-Neo digested by KpnI and PstI were analysed on Southern blot, these dilutions correspond to 0.1, 0.5 and 1.0 copies of plasmid, respectively, for 10 μg of genomic DNA.

Furthermore, the DNA of the infected cells not selected by neomycin was systematically placed side by side in order to quantify the infectivity of the construction; the cells which had undergone selection constituted an infection control of 100%, Titration: Infective viral titers by viral dilutions Successive dilutions of the primary supernatant were used to infect NIH3T3; undiluted supernatant, supernatant diluted 1/10, 1/1000 and 1/100000. The cells are infected by a viral supernatant in the proportion of 0.5 ml per well 35 mm in diameter; the selection drug is added precisely 20 hours after infection directly on to the culture dish without trypsinization of the cells. The infective titer selected corresponds to the number of colonies observed for the last dilution at which colonies appear, multiplied by the inverse of this dilution.

In the case of the first clone the titer of initial producer cells is $2\times10^6$ pfu/ml. In the case of the second clone the titer is $10^6$ pfu/ml.

The two producer clones were frozen normally in order to conserve initial passages on the one hand; and on the other, maintained in continuous culture for several months. The successive titrations (dilutions of the viral supernatant) made it possible to identify a progressive diminution of the titers. In the case of the first clone, the titer passed from more than $2\times10^6$ to only $10^1$ in the interval of two months' continuous culture, this drastic fill in the titer was accompanied by a change in the growth of the cells in culture with a concentric appearance and ease of detachment. In the case of the second clone, the titer passed from more than $10^6$ to $10^5$ in an interval of two months' of continuous culture, to diminish to $10^3$–$10^4$ after three and a half months; this moderate fall in the titer was not accompanied by any change in the morphology or growth of the cells in culture.

4 Helper activity assay on 3T3BAG

This research was conducted by the mobilization test on 3T3 BAG lines (Danos et al., 1988; Danos, 19912).

The 3T3 BAG cells were infected initially by the undiluted supernatant of infected packaging lines. Several successive cycles of infection of unexposed 3T3 BAG with the supernatant of previously infected 3T3 BAG were carried out to sensitize the assay, which proved to be negative. Furthermore, colonies of cells resistant to neomycin could not be detected after placing the unexposed NIH3T3 in contact with the supernatant of infected NIH3T3 selected by neomycin.

5) INTEGRATION SITES

Human and non-human primate cells were used to identify the number of integration sites of the virus after infection. The mouse cells provide indications of very moderate quality in as much as there exists in these cells a significant background associated with multiple integrations of retroviral or retroviral-like sequences.

For this purpose, monkey VERO cells were infected with several dilutions of viral supernatant. In the case of the dilution $10^{-2}$, independent clones were obtained; each one having been initiated from a single profile of viral integration. The use of a restriction enzyme which cuts within the viral construction, on the one hand, and in the genomic DNA of the cell host at variable distances from the integration sites, on the other, made it possible to obtain as many restriction fragments of variable size as there were integration events. In this case, the enzymes XbaI or SalI were used.

6) STABILITY OF THE VIRAL TITERS—MASTER BANK SYSTEM

A homogeneous stock of cells producing virus was constituted and extensively controlled for the absence of viruses competent to replicate by the following methods:

Mobilization test on 3T3 BAG cells

Amplification on NIH3T3

Intraperitoneal inoculation of newborn mice, in order to study a possible in vivo pathogenesis.

Starting from this cell bank ("Master Cell Bank" MCB) a working cell bank was constituted. The viral titers obtained remained stable for several months and were of the order of $20\times10^6$ to $3\times10^7$ cfu/ml (the initial dilutions having been grown systematically only at $10^{-6}$). Results were also obtained with an assay including a dilution at $10^{-7}$. The titers are remarkably stable for several months at this level of intensity.

B) ADDITONAL RETROVIRUS CONSTRUCTS

A construction was made with a still more reduced LTR upstream from the 3' LTR in particular; designation FOCH29-PL (for FOCH29 pure LTRs) shown in FIG. 2.

This construction made it possible to assess the advantage in terms of genetic stability of the excision of the 140 bases, including 104 of the end of the envelope upstream from the viral LTRs.

The construction was made from the plasmid pUC19 including the EcoRI-PvuII fragment described in part Bl-l: enzymatic cutting by the restriction enzyme EspI (or IsoCelII) at position 7864 (namely +23 of the viral LTR). At the 5' end the bases generated by a EcoRI cut were artificially added to a double stranded synthetic oligonucleotide complementary to the 23 bases of the LTR (140 bases, 103 of which are bases of the envelope). At the 3' end the oligonucleotide is complementary to the cohesive SpeI ends. The oligonucleotide sequences are the following: oligo-SENSE 5'-AAT TCA ATG AAA GAC CCC AAA TTG C-3' SEQ ID NO: 5, oligo-ANTISENSE 5'-TAA GCA ATT CGG TGG GGT CTT TCA TTG-3' SEQ ID NO: 6.

C) CONSTRUCTS INTENDED FOR COMPLEMENTATION PASSING THROUGH PACKAGING CELL-LINES

1) GAG-POL construct towards finalizing an original packaging cell-line.

The various steps involving the use of Friend virus FB29-strain derived sequences are hereunder described.

The complementing gag/pol construction for the nucleocapsid proteins and the reverse transcriptase is derived from the FB29 strain of the Friend virus.

The basic construction was assembled from the construction described in the paragraph in which the LTR was left in place or replaced by the sequences of the RAR-beta promoter.

A large deletion of the packaging sequences situated upstream from the sequences coding for the gag capsid nucleoproteins (starting at +619) is carried out as follows: SpeI (or IsocelII) cut, unique site at +280; and PstI at +560–561 which removes 280 bases. A synthetic linker SpeI-PstI is synthesized 5'-CTAGTGCA-3' SEQ ID NO: 7 and annealed to the plasmid, cut again by HindIII. Ligation is then carried out with the third fragment PstI-HindIII including the major part of the gag and pol sequences.

Alternatively, the synthetic SpeI-PstI adaptator has been merely replaced by a PstI linker.

Then, in a second step (after transformation and selection of the positive recombinants), the PstI—PstI (561–737) including the ATG of GAG was cloned at the PstI site in its original position in order to reestablish the totality of the gag sequences; the orientation of the cloning of this small symmetric PstI—PstI fragment is established by enzymatic digestion with HaeII (position 720; a second site is situated at 4291 but does not disturb the orientation)/AhaIII (unique site in the entire FB29 sequence at position 1031) or EspI (unique site in th entire FB29 sequence at position 7864 of the LTR). As a result of the method used for the cloning at the HindIII site of pUC19 of the DNA sequences corresponding to the entire FB29 genome, the end of the pol sequences was recovered as follows: initial cut by HindIII (5060) and SnaI (=iso BstII07I) (unique site at 6335); after purification, this fragment was cut again by SmaI (6079) to produce a fragment of 1019 bases comprising a minimum of envelope sequences (244 bases). This fragment was subcloned in the HindIII-HincII of the polylinker of pUC18. The polyadenylation signal of SV40 was juxtaposed downstream (excised from the plasmid pCRIPgag-2, Danos and Mulligan, 1988) from the construction.

A NheI on the 5'-end and EcoRI on the 3'-end fragment is excised from a SV40-polyA containing plasmid, including the HpaI-EcoRI (position 2666 to 1782) fragment of SV40 early promoter polyadenylation signal. This fragment is further cloned [at the XbaI (NheI-cohesive-or else through XbaI partial digest since an XbaI restriction site maps at this end of Friend pol); or else as a preliminary step before cloning the end of pol in pUC18) or blunt or following insertion of a SpeI linker (cohesive to NheI restriction) at the KpnI site of pUC18 polylinker] and dowstream, EcoRI cohesive.

Figure 3A:
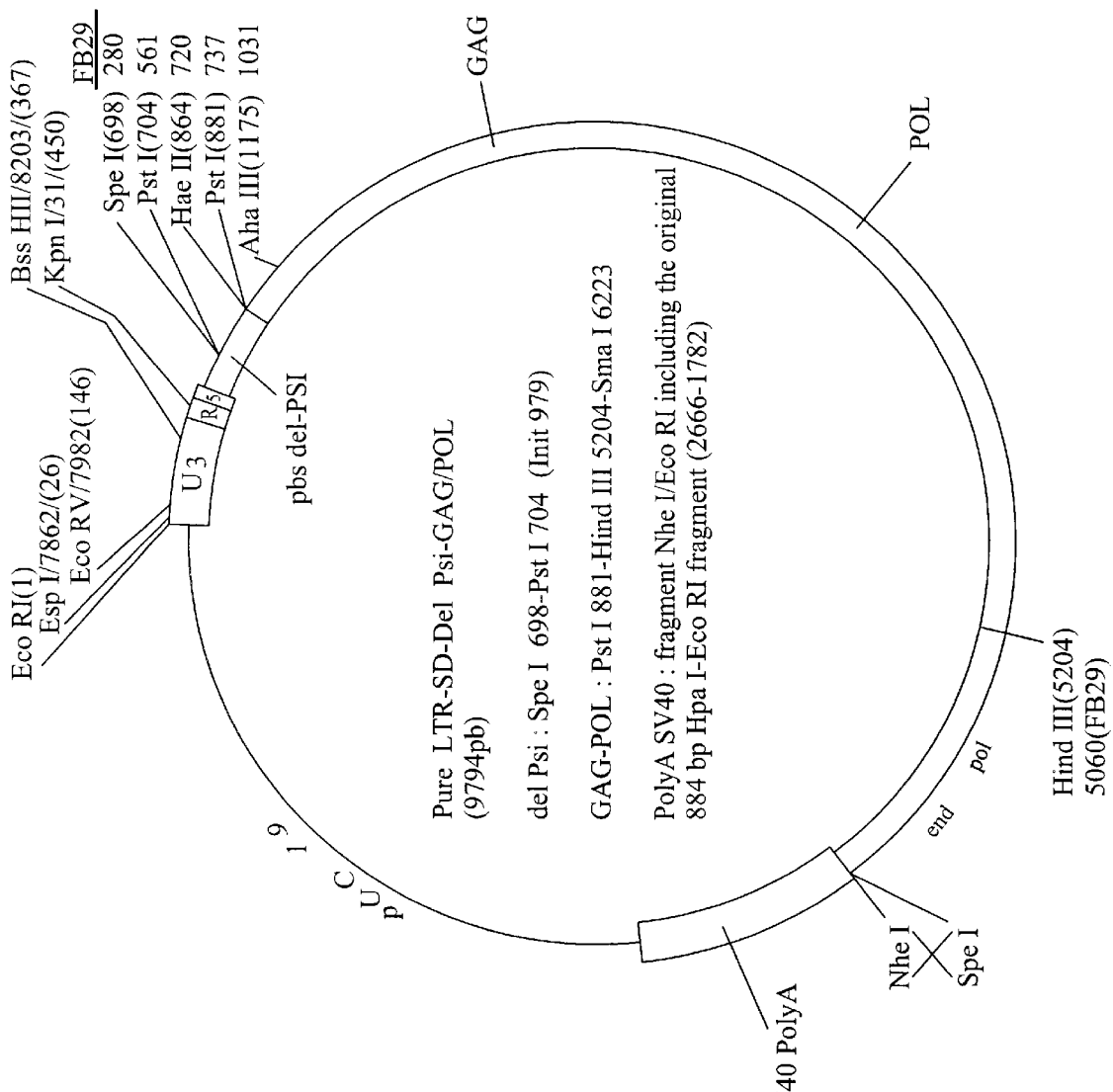
Figure 3B:
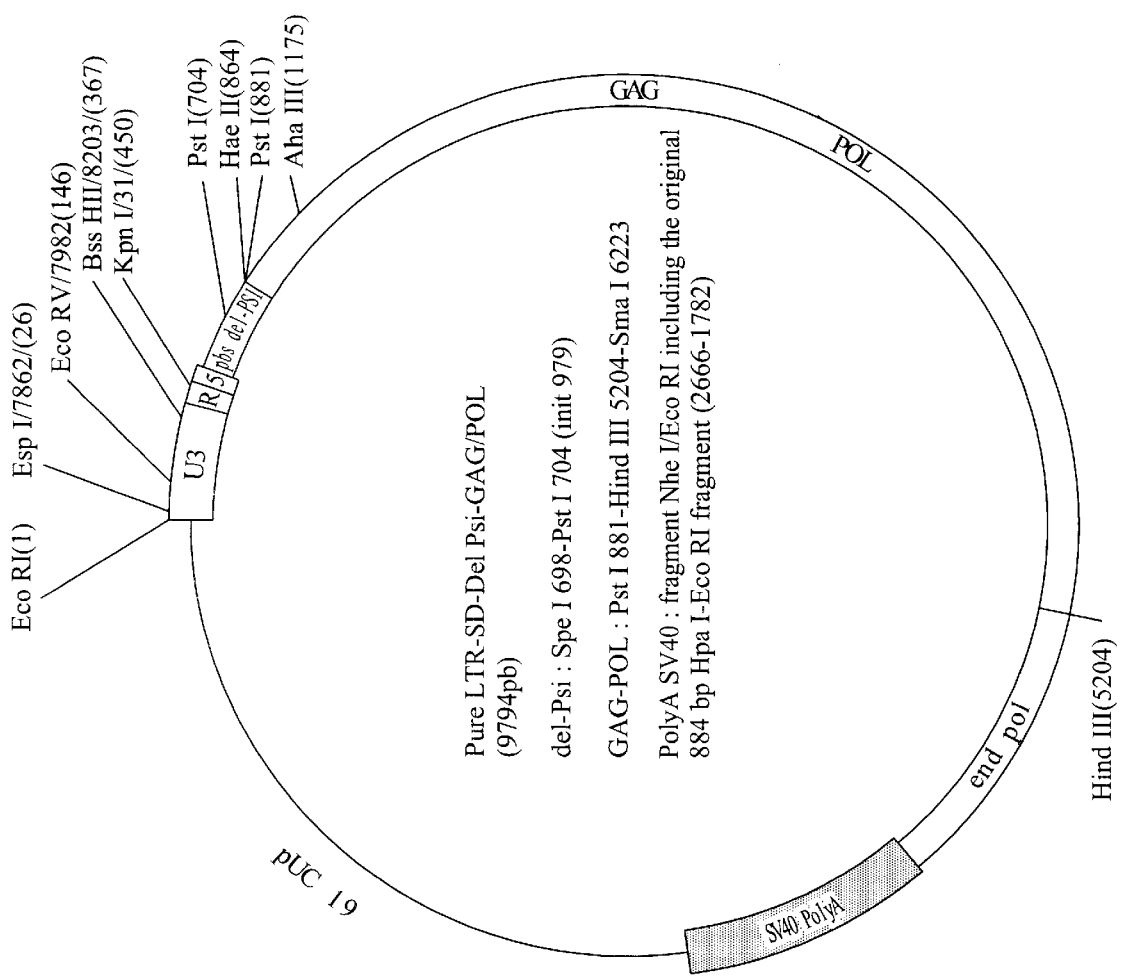

The POL and polyA sequences were excised as a unit from pUC18 by means of 5'-HindIII and 3'-EcoRI restriction and ligation was carried out with the plasmid pUC19/pure LTR/del-psi/GAG/2/3-POL, described in the above paragraph (FIG. 3)

Figure 4A:
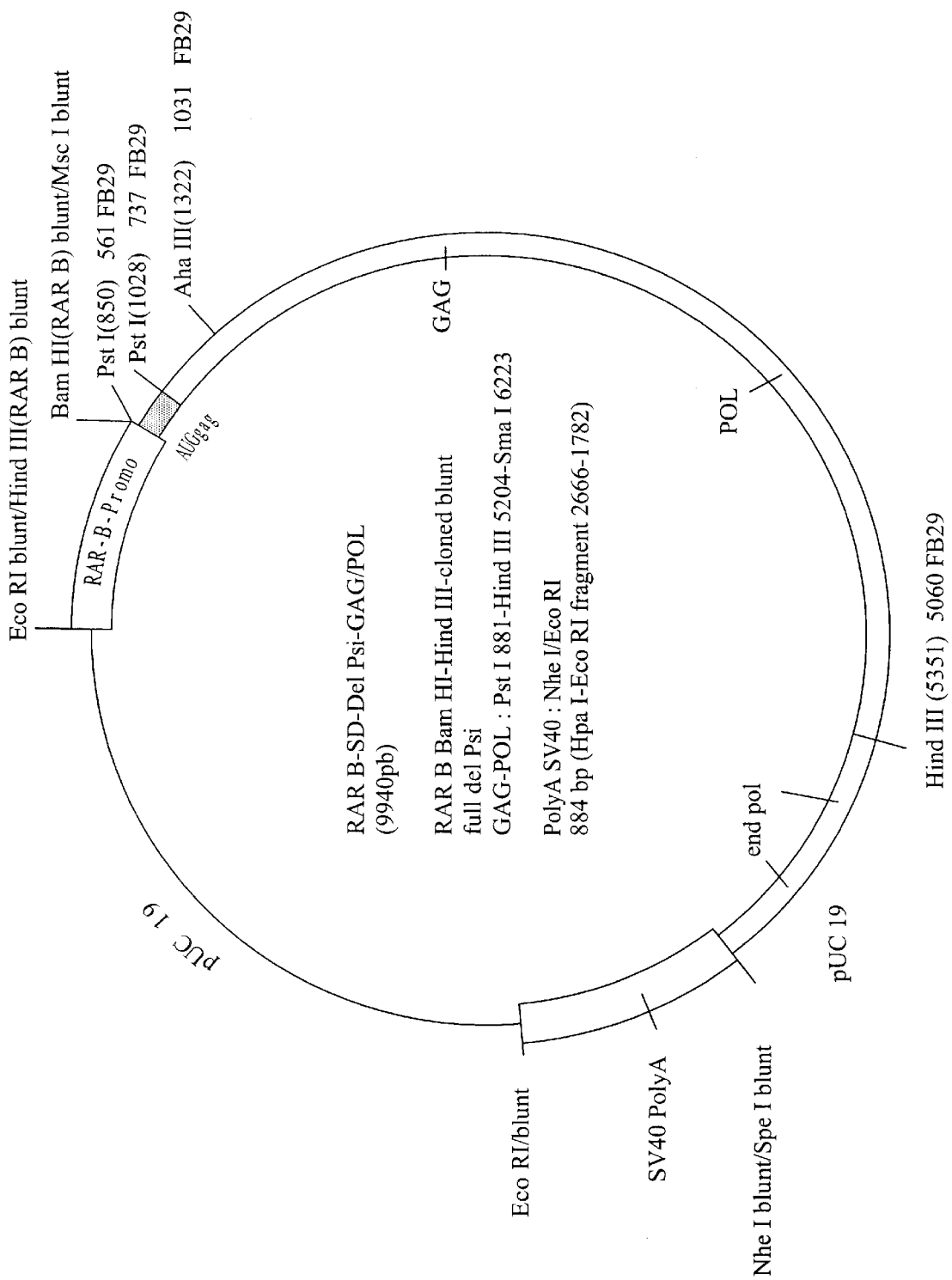

A similar construct can be established in replacing the viral LTR by a non-viral promoter such as RAR-β (FIG. 4A).

Figure 4B:
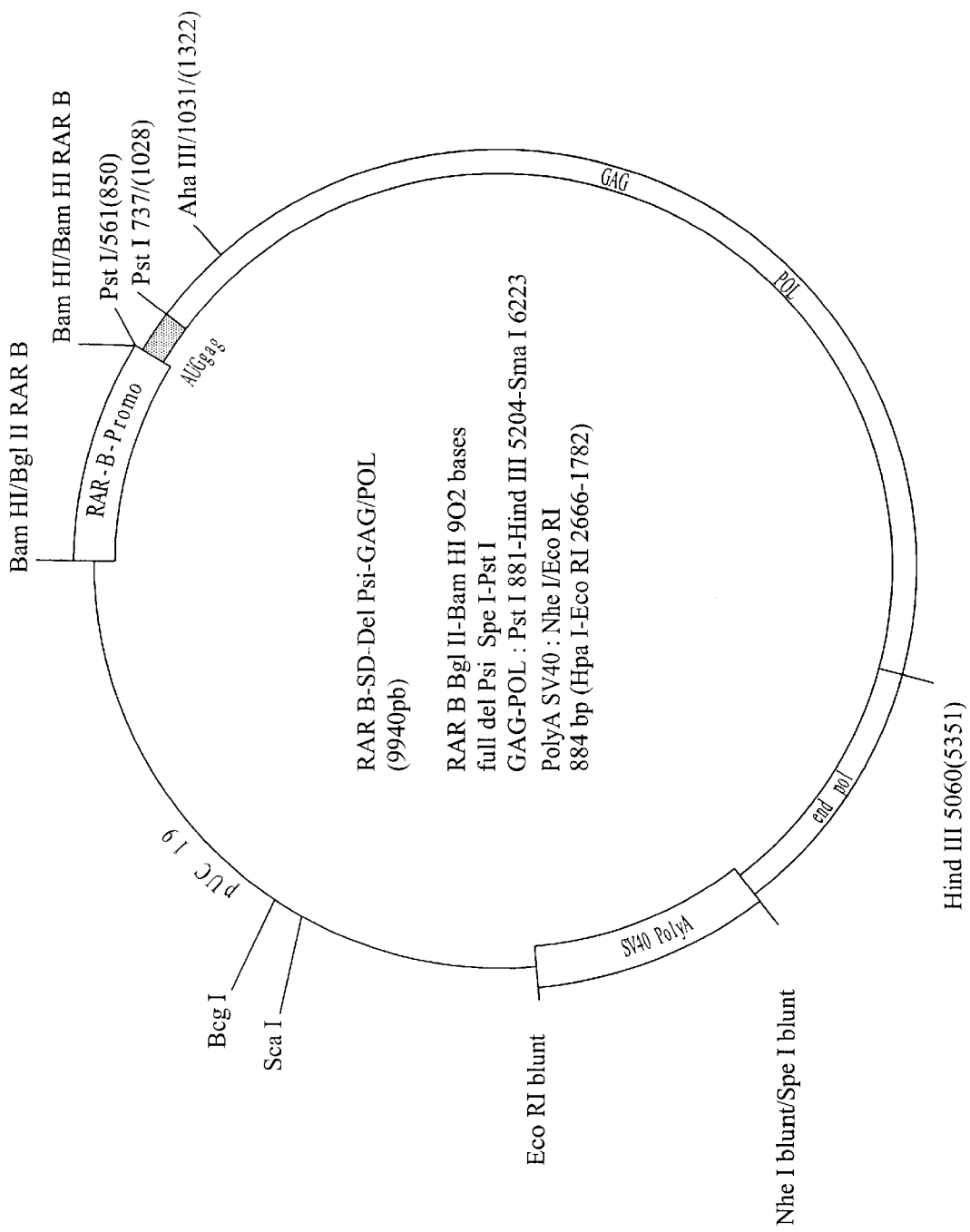

In that setting, the BglII-BamHI fragment of RAR-β promoter is cloned into the BamHI site of pUC19 (the BglII-BamHI fragment harbouring two BamHI-cohesive ends). The correct orientation is identified taking advantage of the EcoRI site 85 bases upstream of the BamHI site (3'-end) which generate two non-symetric fragments from the RAR-β promoter. This plasmid is further opened at either BcgI or ScaI in 5' and AflIII (3') in order to purify in a second step the BcgI or ScaI/PstI (3') fragment which comprizes the RAR-β promoter (respectively 1803 or 1841). Unless the fragment is primarily isolated by means of an AflIII digestion (respectively 2200 and 2250 bases), separation of the fragments generated by PstI cutting is impossible. The purified fragment is further ligated to the PstI/ScaI or BcgI fragment which has been excised from the LTR-GAG/POL plasmid. The latter includes the gag/pol sequences cleared of the viral LTR (7837 or 7875 bases). The construct is completed in restoring the 176 bp PstI—PstI gag fragment by means of opening the previous construct with PstI and cloning the small fragment in an orientated fashion (already described above) (FIG. 4B).

Figure 5:
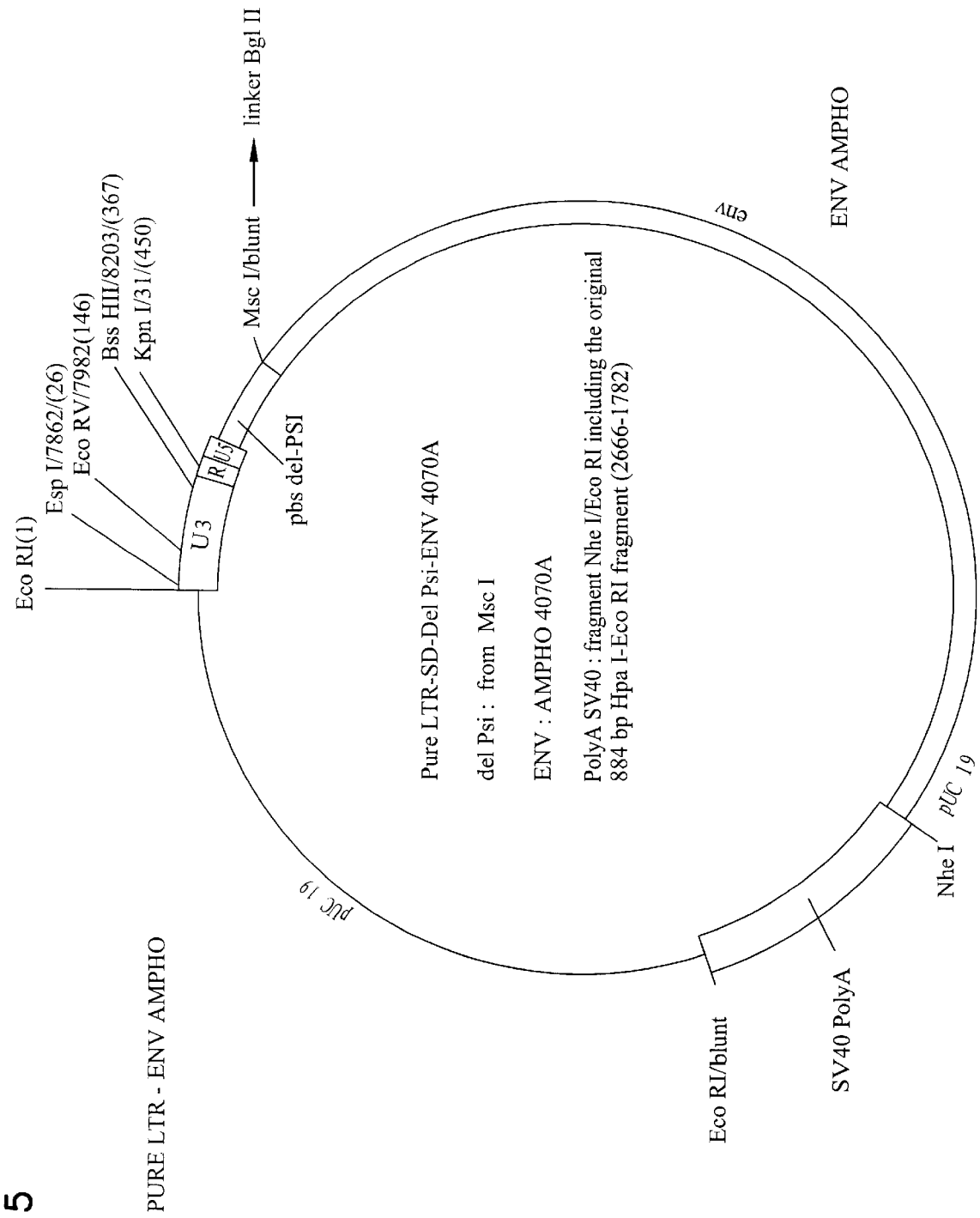
Figure 7A:
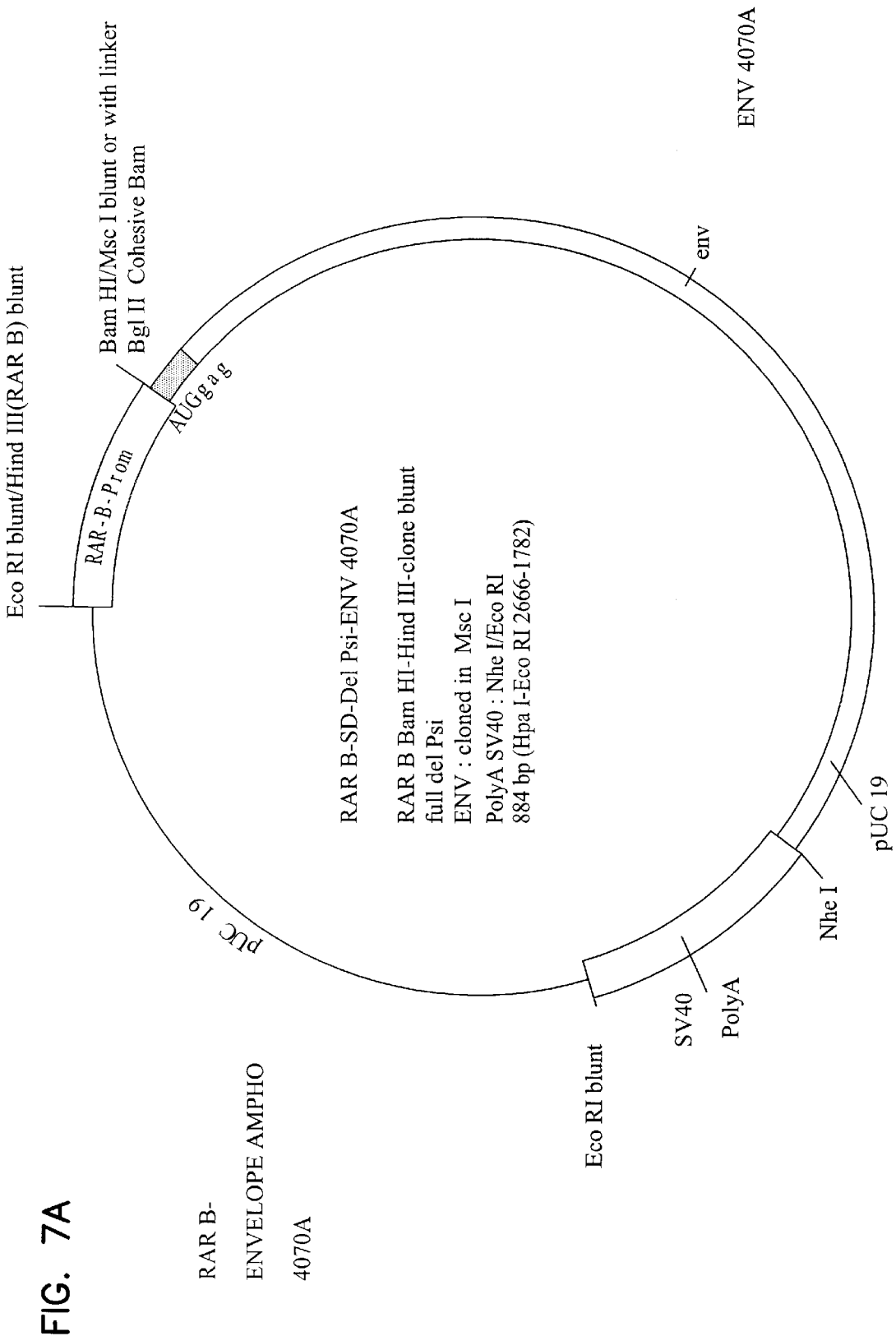
FIGS. 7A and 7B are construction of the plasmid-vector RAR-β including the 4070A amphotropic envelope.
Figure 7B:
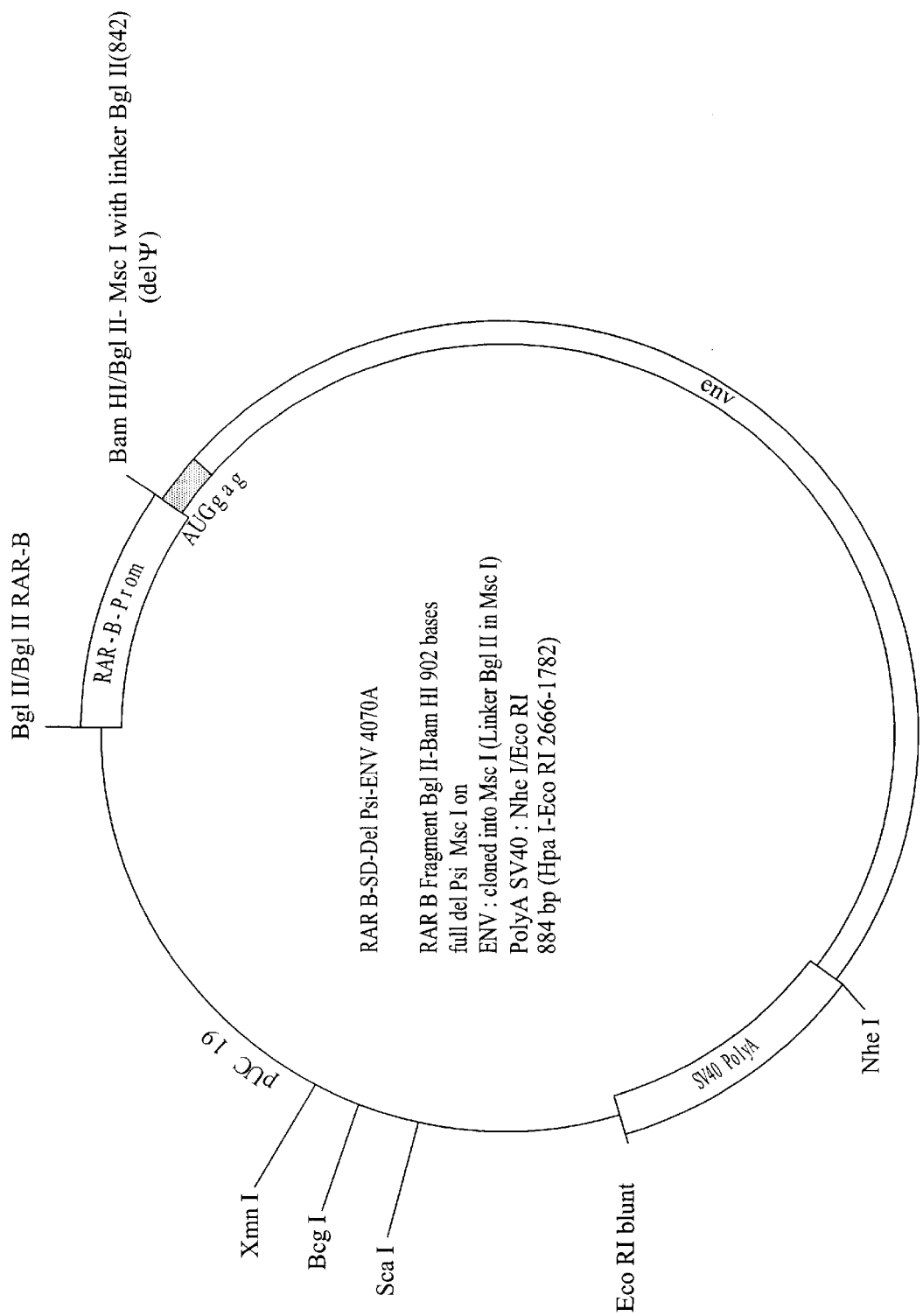

2) Amphotropic ENV-construct (FIGS. 5 and 7)

The 4070A amphotropic envelope sequences, derived from an amphotropic strain of Moloney leukaemia virus (Mo-MuLV) (Chattopadhyay et al., 1981), similar to those used in the Psi-CRIP cell-line are being used towards envelope complementation. Tranfection is performed in co-transfecting with a second gene allowing for selection such as with histidinol or hygromycin.

Two options are being considered:

a) Transcription driven off a viral 5'LTR with a downstream polyadenylation site from SV40: a BglII-EcoRI fragment is excised from pCRIPAMgag-construct, and further ligated to 'pure LTR' construct, following insertion of a BglII linker at the MscI site of the FB29 sequence, towards cohesive cloning at the 5'-end, and XbaI blunt (vector)-EcoRI blunt (end of SV40-polyA signal) at the 3'-end.

b) Transcription driven off an inducible promoter which can be triggered using pharmacologic treatment, in particular the abovedescribed retinoic acid β-receptor promoter: where envelope sequences are replacing gag/pol sequences inside the construct which is described in section C where SV40-PolyA sequences are kept. In practice, the viral LTR is excised from the construct described in section a) by means of BglII restriction which releases a cohesive end to that of retinoic acid receptor (BamHI at the 3' end, BglII-cohesive).

The RAR-β amphotropic envelope can be finalized as follows: the construction has been undertaken using an experimental shortcut taking advantage of the 'LTR-env ampho-SV40 polyA' construct. Cloning has been performed as follows: the BglII (−747 site)-BamHI (+155) 902 bases fragment of the retinoic acid β-promoter which includes all transcription regulatory elements of functional benefit, has been purified and cloned into pUC19 in which a BglII linker has been cloned in HindIII. The XmnI (cutting inside pUC19)—BglII fragments derived from both the abovementioned construct and the LTR-env-AMPHO construct (from which the envelope sequences containing fragment is retained) are associated by ligation. The orientation uses the RAR-β fragment EcoRI site; this is made possible since the Amphotropic envelope sequence harbours a distinct additional EcoRI site.

Figure 6A:
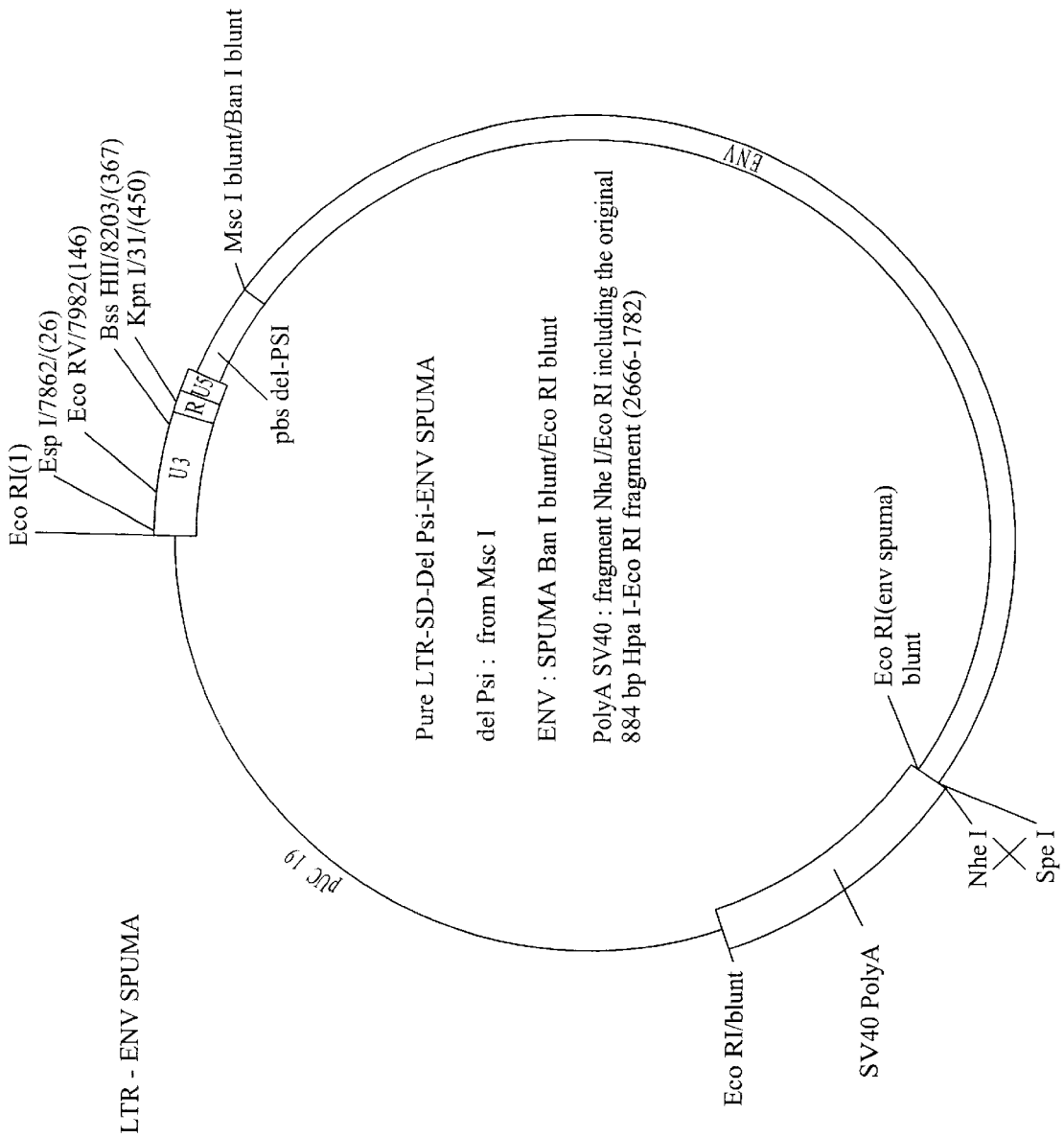
FIGS. 6A and 6B are construction of the plasmid-vector 'Pure LTR' including, the envelope from spumavirus.
Figure 6B:
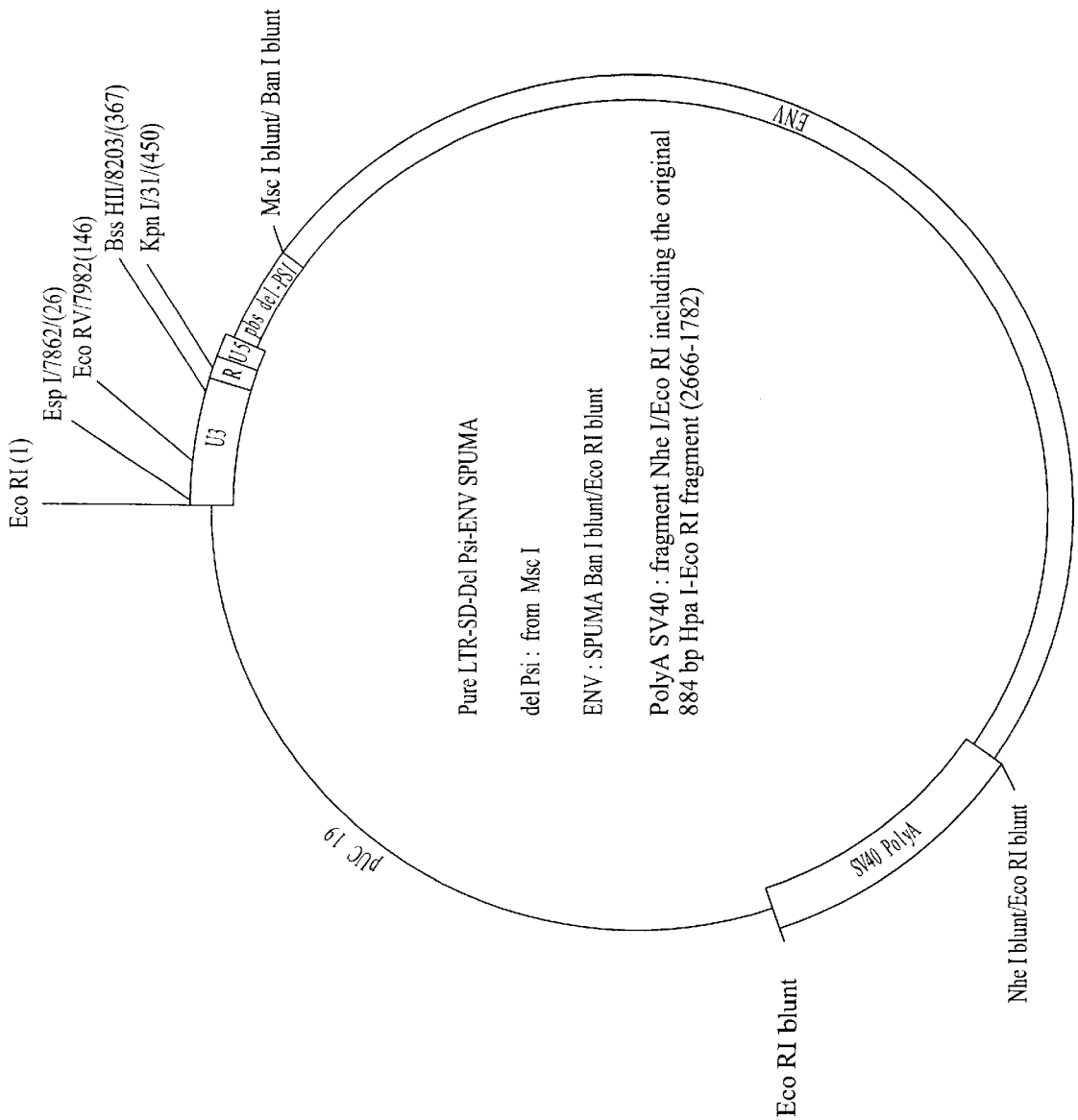
Figure 8A:
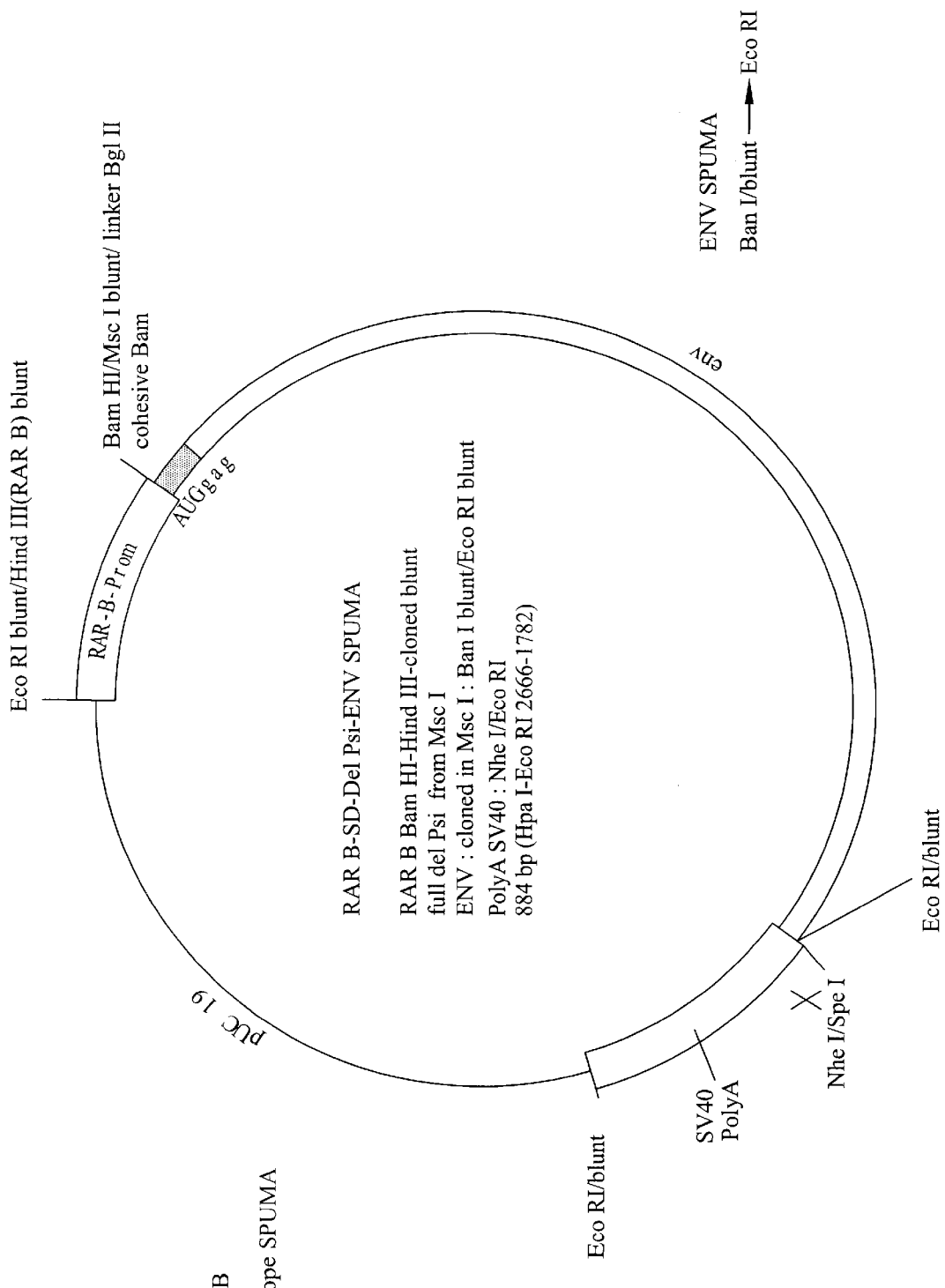
FIGS. 8A and 8B are construction of the plasmid-vector RAR-β including the envelope from spumavirus.
Figure 8B:
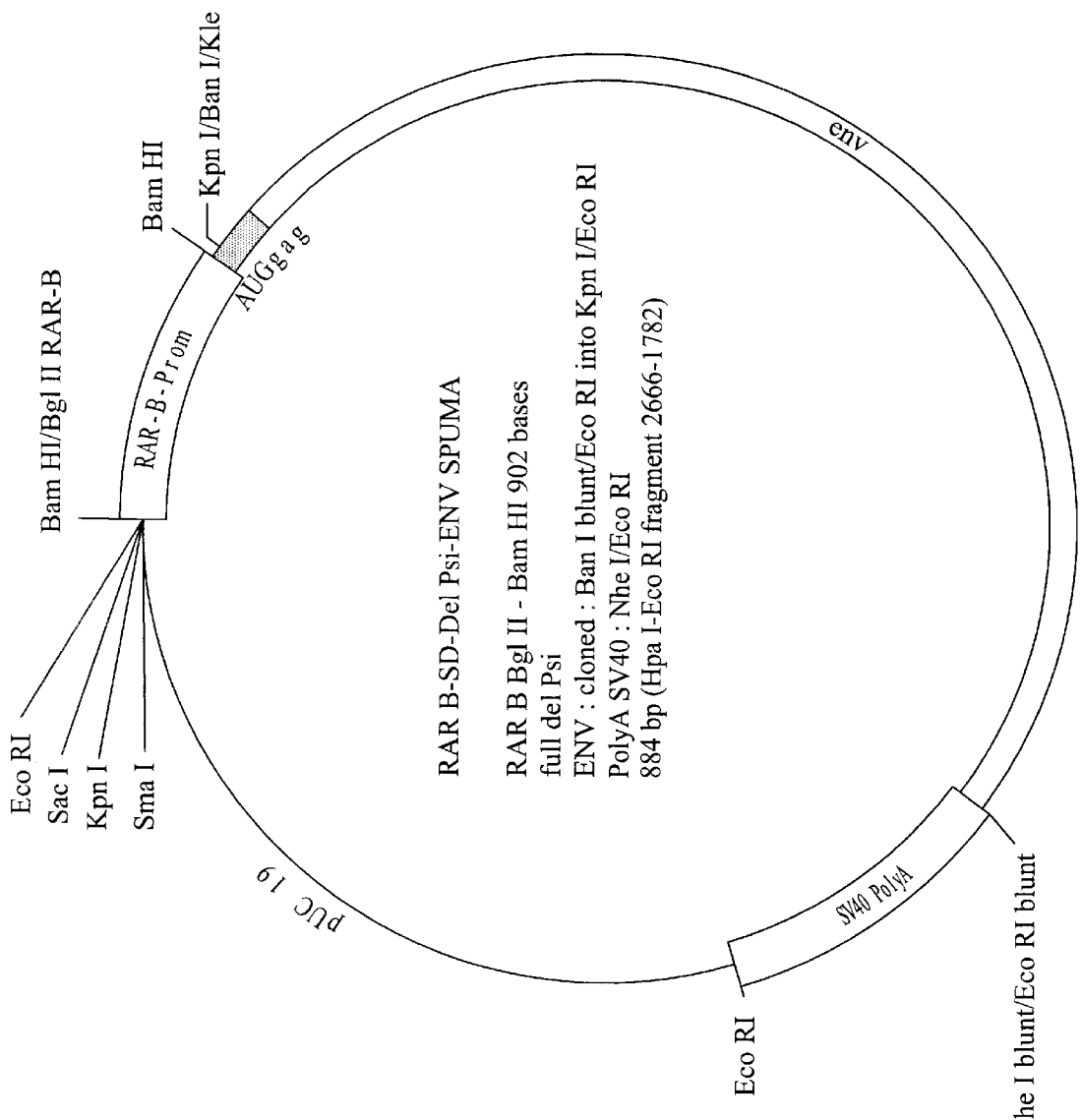

3) Spumavirus ENV-construct (FIGS. 6 and 8)

In a second example, spumavirus envelope sequences have been used.

Spumavirus envelope sequences replace the 4070A amphotropic envelope sequences within the abovementioned constructs; where the SV40-PolyA sequences are being kept.

An EcoRI—EcoRI genomic fragment from spumavirus is sub-cloned at the EcoRI site of pUC19. The fragment under use in the envelope expressing constructs is obtained by means of BanI digestion, which spares 30 base-pairs upstream the envelope-ATG in the spumavirus genome; while the downstream EcoRI site which is close to the termination signal (Flügel et al, 1987) is still used.

Similarly to the amphotropic envelope, two options have been selected.

a) Transcription driven off the 5'-viral LTR with a downstream polyadenylation site from SV40. In order to establish the LTR-spumavirus envelope construct, the EcoRI—EcoRI fragment of the spumavirus envelope is treated with klenow-enzyme and cloned at the HindIII/Klenow-SmaI sites inside pUC18 end pol/polyA-SV40 thus hereby replacing the end of pol. The BanI-EcoRI fragment which includes the spumavirus envelope sequences followed by SV40-polyA is further excised and cloned (blunt: Klenow treatment) into the MscI/HindIII sites (excision of packaging and gag sequences) of the '5'LTR-FB29 pure-LTR' plasmid. The orientation is established by means of digestion with PvuII.

b) Transcription driven off an inducible promoter which can be triggered using pharmacologic treatment, in particular the abovedescribed retinoic acid β-receptor promoter: in order to establish the RAR-β promoter-spumavirus envelope construct, the abovementioned BanI-EcoRI fragment which includes the spumavirus envelope sequences followed by the SV40-polyA is cloned into the KpnI-EcoRI sites of a pUC18 plasmid. The BamHI site inside the polylinker is then opened to clone the RAR-β promoter into it (BglII-BamHI fragment-both ends of which are BamHI cohesive). The orientation is again established taking advantage of an EcoRI site which generates two non-symetrical fragments inside the RAR-β promoter.

At each step, for every construct of interest, a cell-clone is selected according to both level of intensity in the synthesis of the virus complementation proteins and also its stability; a 'Master Cell Bank' is prepared for each selected cell-line.

D) ESTABLISHING PACKAGING CELL-LINES FROM THE DOG FOETAL CELL 'DOG'

D.1. Selection of dog foetal cells

The selection of foetal dog cells is obtained in accordance with the following method:

a) culturing of chosen eukaryotic cells on ISCOVE rich medium (GIBCO) containing, in addition, 10% of foetal calf serum and 10% of horse serum, b) passage of the cultured cells in DMEM medium containing 20% of foetal calf serum and recovery of the selected cells and culture of the cells for one month in a medium without $CO_2$, c) selection of the cells having a rapid growth rate (accelerated kinetics), d) passage of the selected cells in DMEM medium containing 10% of foetal calf serum, e) passage of the cells recovered in step d) in DMEM medium containing 10% of newborn calf serum (HyClone), and f) recovery of the cells selected at the end of step e).

D.2. Packaging cell-lines preparation a) Transfection of the DOG-cell-line with gag/pol sequences (achievement of DOGP29)

Transfection is processed using calcium phosphate precipitation according to standard procedure, without carrier DNA: 10 microgrammes of plasmid have been deposited over a culture dish of 35 mm in diameter where $5 \times 10^4$ cells have been seeded on the previous day.

Cells are grown in Dulbecco's modified Eagle medium (DMEM-Gibco-BRL) containing 10% of newborn calf serum (HyClone). After two days following transfection, cells are trypsinized, 1/20th diluted and placed into selective medium. Those colonies appearing from day 12 are picked up and seeded on 24-well culture dishes in a ratio of one clone per well.

DOGP29 was obtained by transfection of the construction LTR-SD-deletion psi-GAG/POL detailed below (and co-transfection with selection gene, resistance to phleomycin) on dog foetal cell optimized according to the following criteria: 1—absence of endogenous retroviruses; 2—adherent cell; 3—rapid growth; 4—stable and homogeneous morphology; 5—easily transfectable; 6—very high number of passages tolerated (intensive artificial passages for assay); 7—optionally capable of sustaining LTC-IC (Hemato).

A Master Cell Bank System is created from the clone of dog cells selected according to the intensity of synthesis of viral complementation proteins and the stability of expression of the reverse transcriptase (POL).

Packaging cell-lines have been evaluated according to the following evaluation algorithm:

Primary evaluation—proof of efficacy

Second evaluation—selection of stable cell-lines harbouring the upmost accurrate level of expression of viral proteins for the transcomplemention of the defective retroviral vector carrying the gene of interest.

In both instances the methodology under use is identical but in the second case issues relating to quantitative evaluation as well as stability are being considered.

Evaluation strategy using in combination:

1°/Molecular evidencing of the presence of the requested sequence

The latter relies on polymerase chain reaction (PCR) using primers specific for the viral transcomplementing proteins encoding sequences. The primers used are as follows:

gag-sequences (Friend virus FB29-strain)

JB 2008-S TGA CGG GAG AAG AAA AAC AGC G SEQ ID NO:8

GAG-R TAG GAG CAA CTG GCG ATA GTG G SEQ ID NO:9 pol-sequences (Friend virus FB29-strain)

POL-F GAT TGC CAG ACT TGA CTA AGC C SEQ ID NO:10

POL-R TAC CAT CCG TAG GCA AGG SEQ ID NO:11 env-sequences (4070A amphotrophic envelope from Moloney virus)

AMPHO-F ATA CCA ATC ATT CCA CCG CTC C SEQ ID NO:12

AMPHO-R GTT GAG GTC TGT CTG GAT AGC G SEQ ID NO:13 env-sequences (spumavirus HFV or HSRV)

HFVENV-F TAG GAC CTG TAA TAG ACT GG SEQ ID NO:14

HFVENV-R CCT TGA GAA CTC CAA TCC TTC G SEQ ID NO:15

2°/Evidencing functional efficacy of the basic construct deleted of the packaging signal, intended at expressing GAG/POL proteins Transfection of gag/pol constructs into DOGP29 cells; using co-transfection with a plasmid carrying a gene allowing selection.

Expression of POL: the latter is being tested by a reverse transcriptase assay

Expression of GAG: the latter is tested by means of western blot performed on cell-lysates: the antibody used in this assay is a goat polyclonal serum specific for GAG-CAp30 proteins (according to standard techniques).

3°/Inducibility of expression of sequences driven off the retinoic acid β receptor-promoter Cells are being treated by all-trans retinoic acid (ATRA) at a concentration of 10-6 M; the induction is best evaluated in the 24 to 48 hours following addition of ATRA.

4°/Pseudotyping of viral particles, of defective retroviruses derived from murine viruses (in particular Moloney or Friend leukemia inducing viruses) with spumavirus envelope EXPRESSION of spumavirus envelope in packaging cell-lines:

Western blot using an antibody specific for HSRV envelope

Immunofluorescence on envelope expressing cells

INFECTION of target cells:

transmission of genetic sequences carried by a defective retroviral vector derived from murine viruses (in particular Moloney or Friend leukemia inducing viruses) to naive cells by means of HSRV-envelope-mediated viral infection.

The best DOG gag/pol (DOGP29) clones are selected according to measurement of reverse transcriptase activity according to the following protocol where only particularities are quoted, the remaining conditions being known by the expert:

Samples including DOGP29 cells supernatant are loaded into a 96 wells dish in 50 μl (multichannel pipet).

The following samples are used as control of radioactivity: $H_2O$, VIH+, control cells or donor lymphocytes culture supernatant.

Add 10 μl buffer A (KCl=0.5M DTT=50 mM Triton X100=0.5%)

Then 40 μl buffer B (10 μl EGTA 5 mM in TRIS HCl 0.5 M pH 7.8 1 μl $MgCl_2$ 0.5M, 3 μl 3HdTTP (1 mCi/ml) 10 μl polyrA-oligo dT 5 OD/ml 16 μl of water)

Samples are incubated 1 hour at 37° C. Then add 20 μl of buffer C [$Na_4P_2O_7$ 120 mM in 60% TCA]. After 15 minutes at +4° C., the oven is turned on at 60° C. The vacuum pump, the injector and the SKATRON (filter) are turned on. Volumes are being checked. Alcohol is set up on channel 2, water on 1 and the decontamination solution on 3. The skatron is then turned in 'manual' position and washing.

1. channel 3: decontamination solution (TFD4 2%) during 5 seconds twice
2. air
3. alcohol: 20"
4. air
5. distilled<water: 20 to 30 seconds The water cap is put on TCA and that of alcohol on water. Filters are dried in the oven at 60° C.

Filters are further cut and placed in dedicated tubes where 2 ml of scintillation solution are then distributed. In case tubes cannot be analysed immediately they can be placed at +4° C. Data are read by a computer and data given in cpm. The coulter might also provide average of 4 wells.

| Buffer A | |
|---|---|
| KCl (potassium chloride) 0,5M | 7,45 g |
| DTT (dithithreitol) 50 mM | 1,54 g |
| Triton X100 --> 0,5% | 1 ml |
| Sterilized distilled water | to 200 ml |
| Keep at +4° C. | 10 μl per test |
| Buffer B | |
| EGTA 5 mM in TRIS 0,5M pH 7,8 | 10 μl |
| $MgCl_2$ 0,5 M | 1 μl |
| 3HdTTP (1 mCi/ml) | 3 μl |
| poly rA-oligo dT 5 OD/ml | 10 μl |
| Sterilized distilled water | 16 μl |

To be prepared extemporeneously in the appropriate amount, 40 μl for a single test Buffer C ($Na_4P_2O_7$ 120 mM in 60% TCA)

Weigh 10.7 g of PpNa (=sodium pyrophosphate= $Na_4P_2O_7$, 10 $H_2O$)

Add 120 g TCA (trichloracetic acid)

Sterilized distilled water to 200 ml

Keep at +4° C.

Skatron washing buffer (sodium pyrophosphate 1.2 mM in 5% TCA)

Weigh 21.4 g Na4P2O7 (10 H2O) (sodium pyrophosphate)

Add 200 mg pure TCA

Sterilized distilled water to 4 liters (3800 ml)

Optimized reverse transcriptase activity assay:

An optimized assay for the detection of reverse transcriptase of murine leukemia inducing viruses consists in performing the polymerisation reaction not in a magnesium chloride containing buffer (such as abovedescribed and according to molecular biology manufacturers catalogs) but in the presence of manganese (Maniatis, Molecular Biology, A Laboratory Manual, Cold Spring Harbour, 1990).

The protocol is as follows: mix 50 μl of culture supernatant to be tested for reverse transcriptase activity, with 50 μl of a 2× solution containing the following elements: Tris pH 8.3 0.1M; DTT 25 mM; $MnCl_2$ 1.2 mM; NaCl 125 mM; NP40 1/1000; dTTP 0.02 mM; dTTP alpha-32 P (SA: 3000 Ci/mmol) 10 μCi/mmol) 10 μCi/ml; Oligo dT-PolY rA 20 μg/ml; and H2O to requested volume. Samples are incubated during 3 hours at 37° C. Each reaction is filtered on a Whatman DE81 paper, using a dot-blot apparatus; two sheets of Whatman 3MM paper are placed under the DE81. Several washings are performed three times in 2× SCC using the slot blot: then the filter is washed on its own three times 10 minutes in 2× SSC. The filter is finally washed twice one minute in EtOH 95% and immediately dried. The filter is then exposed to a film using amplifying screens.

b) Transfection of the DOGP29-cell-line with env sequences

Transfection is performed under the same conditions as described for the gag/pol construct.

Two different constructs have been established:

the first one (DOGP29L for LTR) where expression of spumavirus envelope is driven off FB29-LTR the other one where expression is driven off an inducible promoter, in particular the retinoic acid β-receptor promoter (eventually associated to HSV-thymidine kinase gene enhancer, in case the expression of the envelope would prove insufficient.

As an example, the retinoic acid β-receptor promoter is used (promoter RAR-β).

A 5'-HindIII and 3'-BamHI fragment of the retinoic acid β-receptor promoter (de Thé et al, 1990) is inserted inside the entirety of the constructs established. From the above-described construct, a BglII linker is inserted at the MscI site of FB29 and the 5'-HindIII and 3'-BamHI fragment of the retinoic acid β-receptor promoter is placed upstream the gag/pol sequences lacking the packaging signal.

c) Selection of DOG29 gag/pol/env for spumavirus envelope

This selection is performed by means of an immunofluorescence assay using anti-spumavirus envelope antibodies.

In a first step cells, histological sections are prepared and further submitted to fluorescence activated cell-sorter analyses (FACS).

Another mode of selection consists in performing a Western blot.

d) Functional assays assessing infectiousness of gag/pol and env cell-lines

Assays establishing infectious properties involve an initial transfection step with a defective retroviral vector including a selection gene. Such a vector has been described in section A.

Infection of NIH3T3 fibroblasts the infection has been performed with the culture supernatant of cell-culture well grown to confluence according to the technique described in section A-4.

Polymerase chain reaction (PCR)

It has been performed according to the technique described in point 5 of section A.

The primers used are the following:

5'-TAAGCAATTCGGTGGGGTCTTTCATTG-3' (oligonucleotide sens) et SEQ ID NO:16

5'-CTGCTGACGGGAGAAGAAAAAC-3' (oligonucleotide antisens) SEQ ID NO:17

Establishing virus titers following transfection with a defective retrovirus vector including a selection gene The chosen method has been described in point 6 of above section A, except for the selection step which has been performed as follows: 20 hours following infection, cell-selection is initiated by adding G418 (1 mg/ml) to the supernatant.

Number of copies transmitted

In addition to the standard titration assay on NIH3T3 an alternative titration method has been proposed fitting in particular the situation where optimized defective retrovirus vectors do not carry any selection gene inside the construct. The titration is then based on molecular methods; in particular, quantitative measurement of the average number of retroviral vector genome copies transmitted using southern blot. The latter does carry DNA from infected cells hydrolysed by a restriction enzyme chosen according to its ability to cut inside each LTR of the retroviral construct complemented by the cell-line of interest (for instance: KpnI); appropriate dilutions of the plasmid including the retroviral construct under consideration are being digested using the same restriction enzyme and placed on the same blot.

SOUTHERN BLOT

Two days after infection by the undiluted supernatant the NIH3T3 were trypsinized, subcultured at about ¹⁄₂₀ on three culture dishes 100 mm in diameter, one of which is subjected to selection by geneticin. At confluence, the genomic DNA of the infected cells for each of the two clones after or without selection is extracted then quantified. The DNA was digested by two restriction enzymes, PstI and KpnI, in order to carry out a Southern blot. After control of the quality of the digestion and the deposition of an equivalent quantity of DNA in each well, the transfer was carried out on a nylon Hybond N membrane (Amersham). Hybridization was performed with a probe which included all of the viral LTR sequences flanked by 100 bases upstream and 100 bases downstream. The probe was labelled by primer extension (Feinberg and Vogelstein, 1983, 1984) with alpha-$^{32}$P labelled dCTP of specific activity of $5 \times 10^8$ cpm/ug. The hybridization was carried out in a medium consisting of: 50% deionized formamide, 5×SSEP; 1×Denhardt's; 5% dextran sulfate and 0.2 mg/ml of sonicated salmon DNA for 20 hours at 42° C. Brief rinsings were carried out in a solution of low stringency: 2×SSEP/0.1%SDS, 5 min at room temperature and 10 min at 65° C.; followed by exposure for 3 days to Kodak-XAR-5 films at –80° C. with LI-Plus intensifying screens (Dupont-NEN).

Search for the production of helper virus

This search was carried out according to description in point 7 of above section A.

REFERENCES

ANDERSON W F, MCGARRITY G J, MOEN R C. Report to the NIH Recombinant DNA Advisory Committeee on murine Replication—Competent Retrovirus (RCR) assays (Feb. 17, 1993). Hum Gene Ther, 4:311–321, 1993

CHATTOPADHYAY et al. J Virol., 39: 777, 1981

COHEN-HAGUENAUER O. Regulation of gene therapy in Europe: a current statement with reference to US regulation Eur J of Cancer, 1994; 30A: 1193–1201

CORNETTA K, MORGAN R A, ANDERSON W F. Safety issues related to retroviral-mediated gene transfer in humans. Hum. Gene Ther. 2: 5–14, 1991

DANOS O, MULLIGAN R C. Safe and efficient generation of recombinant retroviruses with amphotropic and ecotropic host ranges Proc Natl Acad Sci USA 85: 6460–64, 1988

DANOS O. Construction of retroviral packaging cell lines In "Methods in Molecular Biology,: Practical Molecular Virology: viral vectors for gene expression" Collins M Ed., the Humana Press Inc., Clifton, N.J., 1991, 8, pp 17–27

DONAHUE R E, KESSLER S W, BODINE DET A L. Helper virus induced T cell lymphoma in non-human primates after retroviral-mediated gene transfer. J Exp Med, 176, 1125–1135, 1992

FLUGEL R M, RETHWILM A, MAURER B, DARAI G. Nucleotide sequence analysis of the env gene and its flanking regions of the human spumaretrovirus reveals two novel genes. EMBO 6: 2077–2084, 1987

FRENCH ANDERSON W Human gene Therapy Science 256: 808–813, 1992

GUNTER K C, KHAN A S, NOGUSHI P D. The safety of retroviral vectors. Hum Gen Ther, 4, 643–645, 1993

KESSLER D A, SIEGEL J P, NOGUSHI P D, ZOON K C, FEIDEN K L, WOODCOCK J. Regulation of Somatic-cell therapy and gene therapy by the food and drug administration N Engl J Med, 329: 1169–1173, 1993

MATHIEU-MAHUL D, HEARD J M, FICHELSON S, GISSELBRECHT S, SOLA B, LARSENC Viral expression in two myelomonocytic cell lines obtained from long-term bone marrow culture infected with the Friend polycythemia-inducing virus (FV-P) Virology 119: 59–67, 1982

McLACHLIN J R, CORNETTA K, EGLITIS M A, ANDERSON W F. Retroviral-mediated gene transfer Progress in Nucleic Acid Research and Molecular Biology 38: 91–135, 1990

MILLER A D. Human gene therapy comes of age Nature 357: 455–460, 1992

MULLIGAN R C. The basic science of gene therapy Science 260: 926–931, 1993

PERRYMAN S, NISHIO J, CHESEBRO B Complete nucleotide sequence of Friend murine leukemia virus, strain FB29 Nucl Acids Res 19: 6950, 1991

RESTREPO L M, DAL CORTIVO L, HEARD J M, MAROLLEAU J P, MARTY M, BOIRON M, COHEN-HAGUENAUER O, Transduction of haemopoietic progenitors with an original retroviral vector derived from Fr-MuLV with high infection efficiency (soumis, Blood)

SITBON M, SOLA B, EVANS L, NISHIO J, HAYES S F, NATHANSON K, GARON C F, CHESEBRO B. Hemolytic anemia and erythroleukemia, two distinct pathogeneic effects of Friend MuLV: mapping of the effects to different regions of the viral genome Cell 47: 851–859, 1986

SITBON M, ELLERBROK H, POZO F, NISHIO J, HAYES S F, EVANS L H, CHESEBRO B. Sequences in the U5-gag-pol region influence early and late pathogenic effects of Friend and Moloney murine leukemia viruses J Virol 64: 2135–40, 1990

SITBON M, D'AURIOL L, ELLERBROK H, ANDRE C, NISHIO J, PERRYMAN S, POZO F, HAYES S F, WEHRLY K, TAMBOURIN P, GALIBERT F, CHESEBRO B. Substitution of leucine for isoleucine in a sequence highly conserved among retroviral envelope surface glycoproteins attenuates the lytic effect of Friend murine leukemia virus Proc Natl Acad Sci USA 88: 5932–5936, 1991

DE THE H, VIVANCO-RUIZ M M, TIOLLAIS P, STUNNENBERG H, DEJEAN A. Identification of a retinoic acid responsive element in the retinoic acid receptor a gene. Nature 49: 177–180, 1990

TEMIM H M. Safety considerations in somatic gene therapy of human disease with retrovirus vectors. Hum Gene Ther, 1: 11–123, 1990

BUJARD H., Gene Therapy 2: S1, 1995

BURNS J C et al., Proc. Natl. Acad. Sci. USA 90: 8033–8037, 1993

CHATTOPADHYAY S K. et al., J. Virol. 39: 777–791, 1981

EMI N. et al., J. Virol. 65: 1202–1207, 1991

MILLER D. et al., J. Virol. 65: 2220–2224, 1991

WANG Y. et al., Proc. Natl. Acd. Sci. USA 91: 8180–8184, 1994

WILSON C. et al., J. Virol. 63: 2374–2378, 1989 ZAWADA J. et al., J. Gen. Virol. 15: 183–191, 1972.

ZAWADA J. et al, J. Gen. Virol. 15: 183–191, 1972

What is claimed is:

1. A cultured eukaryotic cell exhibiting the following properties:

the cell is selected from a dog, the cell has a homogeneous morphology that is stable over time, the cell is not of tumor origin, the cell is selectable in a minimum culture medium lacking $CO_2$, without prior transformation, and the cell exhibits accelerated kinetics, wherein the cell is suitable for packaging recombinant retroviral RNAs by transcomplementation.

2. The cell of claim 1, wherein the cell is a fetal or embryonic cell.

3. The cell of claim 1, wherein the cell is selected by a method comprising:

a) culturing an eukaryotic cell on ISCOVE rich medium containing, in addition, 10% of fetal calf serum and 10% of horse serum;

b) passing the cultured cell in DMEM medium containing 20% of fetal calf serum, recovering the selected cell, and culturing the cell for one month in a medium without $CO_2$;

c) selecting the cell exhibiting accelerated kinetics;

d) passing the selected cell in DMEM medium containing 10% of fetal calf serum;

e) passing the cell recovered in step d) in DMEM medium containing 10% of newborn calf serum; and f) recovering the cell selected at the end of step e).

4. The cell of claim 1, wherein the cell is a fetal dog cell DOGOM1 deposited at the Collection Nationale de Culture des Microorganismes (CNCM) on Nov. 30, 1994 under number I-1496.

5. The cell of claim 1, wherein the cell is a recombinant cell modified with nucleotide sequences coding for transcomplementing polypeptides and/or glycoproteins, the sequences being supplied by means of at least two vectors; and the cell packages recombinant retroviral RNAs by transcomplementation.

6. The cell of claim 5, wherein the cell is modified by transfection or by infection.

7. The cell of claim 5, wherein the nucleotide sequence of one of the vectors for transcomplementation, codes for envelope polypeptides and is modified by replacement of nucleotides by an arrangement of nucleotides coding for a sequence of a polypeptide or glycoprotein recognized specifically by a defined cell type, or by the addition of such an arrangement.

8. The cell of claim 5, wherein the recombinant cell is further transfected with a retroviral comprising a transgenic sequence, wherein said retroviral vector is the vector pFOCH29 deposited at the Collection Nationale de Culture des Microorganismes (CNCM) under No. I-1326, into which the transgenic sequence is inserted at a site which is non-essential for its replication.

9. The cell of claim 5, wherein the recombinant cell is modified with:

a) a first expression vector for complementation with respect to the envelope, of a retroviral vector for the transfer and/or integration of a nucleotide sequence within the genome of a target cell, said first vector for complementation comprising a nucleotide sequence coding for envelope polypeptides and elements for regulation of the expression of the nucleotide sequence coding for envelope polypeptides; and b) a second expression vector for transcomplementation of GAG and POL polypeptides, of a retroviral vector for the transfer and/or integration of a nucleotide sequence within the genome of a target cell, said second vector for transcomplementation comprising:
A) a gag nucleotide sequence coding for one or more nucleoprotein polypeptides from a Friend retrovirus;
B) a pol nucleotide sequence coding of one or more polypeptides including a reverse transcriptase and an integrase from a Friend retrovirus; and
C) transcription regulating signals controlling the expression of the gag and pol sequences,
wherein the first and second expression vectors lack packaging signals.

10. The cell of claim 5, wherein the recombinant cell comprises:
a) a gag nucleotide sequence coding for one or more nucleoprotein polypeptides from a Friend retrovirus;
b) a pol nucleotide sequence coding for one or more reverse transcriptase and integrase polypeptides from a Friend retrovirus;
c) transcription regulating signals controlling the expression of the gag and pol genes;
d) an env nucleotide sequence coding for one or more amphotropic envelope polypeptides; and
e) non-viral transcription regulating signals controlling the expression of the env sequence.

11. The cell of claim 5, wherein the cell comprises:
a) a gag nucleotide sequence coding for one or more nucleoprotein polypeptides of a Friend retrovirus;
b) a pol nucleotide sequence coding for one or more reverse transcriptase and integrase polypeptides of a Friend retrovirus;
c) transcription regulator signals controlling the expression of the gag and pol genes;
d) an env nucleotide sequence coding for one or more amphotropic envelope polypeptides; and
e) non-viral transcription regulator signals controlling the expression of the env sequence.

12. The cell of claim 8, wherein the transgenic sequence is a nucleotide sequence coding for a gene intended for therapeutic purposes, or for an antisense nucleotide sequence, or for a dominant negative mutant of a gene or a sequence coding for a functional inhibitor of a gene, for a marker gene or for a sequence regulating a gene, or for a gene which adds a novel function to the target cell.

13. The cell of claim 9, wherein the gag and pol nucleotide sequences of said Friend retrovirus are from strain FB29, and wherein said gag and pol nucleotide sequences are under the control of the transcription signals contained in the LTR sequence of the Friend retrovirus strain FB29, and wherein said cell comprises an env nucleotide sequence of a retrovirus of the spumavirus family, which is under the control of an inducible promoter.

14. The cell of claim 13, wherein the inducible promoter is a RARβ promoter.

15. The cell of claim 9, wherein said transcription regulating signals comprise a non-viral promoter.

16. The cell of claim 15, wherein the promoter is an inducible promoter.

17. The cell of claim 16, wherein the inducible promoter is a RARβ promoter.

18. The cell of claim 9, wherein the retroviral vector is a deletion mutant, a substitution mutant, or both, of vector pFOCH29, or is vector pFOCH29.

19. The cell of claim 18, wherein the vector is deleted within the LTR sequence.

20. The cell of claim 19, wherein the vector is pFOCH29PL.

21. The cell of claim 11, wherein the transcription regulating signals controlling the expression of the gag and pol genes are non-viral signals.

22. The cell of claim 11, wherein the env nucleotide sequence encodes envelope 4070A of Moloney leukemia virus (Mo-MuLV).

23. The cell of claim 11, wherein non-viral transcription regulating signals controlling the expression of the env sequence comprise an inducible promoter or a conditional promoter.

24. The cell of claim 23, wherein the inducible promoter is a RAR-β promoter.

25. An expression vector comprising:
a) an env nucleotide sequence coding for one or more polypeptides from a retrovirus of the spumavirus family and permitting the packaging of retroviral RNAs; and
b) transcription regulating signals controlling the expression of the env sequence;
wherein the expression vector is used for transcomplementation of a retroviral vector, which transfers, integrates, or both, a nucleotide sequence within the genome of a target cell.

26. The vector of claim 25, wherein the env nucleotide sequence is from a HSVR spumavirus.

27. The vector of claim 25, wherein the transcription regulating signals comprise a non-viral promoter.

28. The vector of claim 25, wherein the transcription regulating signals are from the LTR sequence of Friend retrovirus.

29. The expression vector of claim 25, wherein the expression vector is an integrative vector.

30. The expression vector of claim 25, wherein the expression vector is used for transfection or infection of human cells in vitro.

31. The expression vector of claim 25, wherein the expression vector is an episomal vector.

32. The expression vector of claim 25, wherein the env nucleotide sequence codes for one or more truncated envelope polypeptides.

33. The expression vector of claim 25, wherein the env nucleotide sequence is modified by replacement of nucleotides by an arrangement of nucleotides coding for a polypeptide or glycoprotein recognized by a defined cell type, or by the addition of such an arrangement.

34. The vector of claim 25, wherein the nucleotide sequence of the expression vector for transcomplementation, coding for the envelope polypeptides, is modified.

35. The vector of claim 27, wherein the non-viral promoter is an inducible promoter.

36. The vector of claim 27, wherein the non-viral promoter is a conditional promoter.

37. The vector of claim 27, wherein the non-viral promoter is a RARβ promoter of a retinoic acid β receptor.

38. The vector of claim 34, wherein the modification comprises replacement of nucleotides by an arrangement of nucleotides coding for a polypeptide or glycoprotein recognized specifically by a defined cell type, or wherein the modification comprises addition of such an arrangement.

39. The expression vector of claim 30, wherein the human cells are endothelial muscle or stromal cells.

40. An expression vector comprising an env nucleotide sequence, coding for the envelope 4070A of Moloney leukemia virus (Mo-MuLV), said env nucleotide sequence being under the control of an inducible promoter.

41. An expression vector comprising an env nucleotide sequence, coding for envelope polypeptides from a retrovirus, said env nucleotide sequence being under the control of a RAR-β promoter.

42. The expression vector of claim 40 or 41, wherein the env nucleotide sequence is modified.

43. The expression vector of claim 42, wherein the modification comprises replacement of nucleotides by an arrangement of nucleotides coding for a polypeptide or glycoprotein recognized specifically by a defined cell type, or wherein the modification comprises addition of such an arrangement.

44. The expression vector of claim 41, wherein the expression vector is an episomal vector.

45. An expression vector comprising:
   a) a gag nucleotide sequence coding for one or more nucleoprotein polypeptides of a Friend retrovirus;
   b) a pol nucleotide sequence coding for one or more pol polypeptides and including a reverse transcriptase protein and an integrase from a Friend retrovirus; and
   c) non-viral transcription regulating signals controlling the expression of the gag and pol sequences,
   wherein the vector is used for the transcomplementation of a retroviral vector, that transfers and/or integrates a nucleotide sequence within the genome of a target cell.

46. The expression vector of claim 45, wherein the non-viral transcription regulating signals comprise an inducible promoter or a conditional promoter.

47. The expression vector of claim 46, wherein said inducible promoter is a RAR-β promoter.

48. The expression vector of claim 25 or 45, wherein the expression vector lacks packaging signals.

49. The expression vector of claim 45, wherein the expression vector is an integrative vector.

50. The expression vector of claim 45, wherein the expression vector is used for transfection or infection of human cells in vitro.

51. The expression vector of claim 50, wherein the human cells are endothelial, muscle or stromal cells.

52. The expression vector of claim 45, wherein the expression vector is an episomal vector.

53. An expression vector comprising an env nucleotide sequence, coding for envelope polypeptides from a retrovirus, said env nucleotide sequence being under the control of the LTR sequence of Friend retrovirus.

54. An eukaryotic cell transformed by a vector of any one of claims 40, 41, 25, 45 and 53.

55. An eukaryotic cell transformed by a vector of claim 34.

56. An eukaryotic cell transformed by a vector of claim 42.

57. An expression vector comprising an env nucleotide sequence, coding for envelope polypeptides from a spumavirus, said env nucleotide sequence being under the control of an inducible promoter.

58. The expression vector of claim 57, wherein the spumavirus is HFV.

* * * * *